US010059746B2

(12) United States Patent
Bishop et al.

(10) Patent No.: US 10,059,746 B2
(45) **Date of Patent: *Aug. 28, 2018**

(54) METHODS OF IMPROVING VACCINE IMMUNOGENICITY

(75) Inventors: Gail Bishop, Iowa City, IA (US); Tony Vanden Bush, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 68 days.

This patent is subject to a terminal disclaimer.

(21) Appl. No.: 14/110,101

(22) PCT Filed: Apr. 4, 2012

(86) PCT No.: PCT/US2012/032190
§ 371 (c)(1),
(2), (4) Date: Oct. 4, 2013

(87) PCT Pub. No.: WO2012/138774
PCT Pub. Date: Oct. 11, 2012

(65) Prior Publication Data

US 2014/0134204 A1 May 15, 2014

Related U.S. Application Data

(60) Provisional application No. 61/471,553, filed on Apr. 4, 2011.

(51) Int. Cl.

| | |
|---|---|
| *A61K 39/13* | (2006.01) |
| *C07K 14/005* | (2006.01) |
| *A61K 39/145* | (2006.01) |
| *A61K 39/29* | (2006.01) |
| *A61K 39/12* | (2006.01) |
| *A61K 39/00* | (2006.01) |
| *A61K 39/385* | (2006.01) |

(52) U.S. Cl.
CPC ............ *C07K 14/005* (2013.01); *A61K 39/12* (2013.01); *A61K 39/13* (2013.01); *A61K 39/145* (2013.01); *A61K 39/292* (2013.01); *A61K 39/385* (2013.01); *A61K 2039/55505* (2013.01); *A61K 2039/6012* (2013.01); *A61K 2039/6037* (2013.01); *A61K 2039/6075* (2013.01); *C12N 2730/10134* (2013.01); *C12N 2760/16134* (2013.01); *C12N 2770/32042* (2013.01)

(58) Field of Classification Search
None
See application file for complete search history.

(56) References Cited

U.S. PATENT DOCUMENTS

| | | | | |
|---|---|---|---|---|
| 3,773,919 A | 11/1973 | Boswell et al. | | |
| 4,559,157 A | 12/1985 | Smith et al. | | |
| 4,608,392 A | 8/1986 | Jacquet et al. | | |
| 4,816,567 A | 3/1989 | Cabilly et al. | | |
| 4,820,508 A | 4/1989 | Wortzman | | |
| 4,873,192 A | 10/1989 | Kunkel | | |
| 4,938,949 A | 7/1990 | Borch et al. | | |
| 4,946,778 A | 8/1990 | Ladner et al. | | |
| 4,992,478 A | 2/1991 | Geria | | |
| 5,071,651 A | 12/1991 | Sabara et al. | | |
| 5,091,513 A | 2/1992 | Huston et al. | | |
| 5,204,096 A | 4/1993 | Neurath et al. | | |
| 5,260,203 A | 11/1993 | Ladner et al. | | |
| 5,350,674 A | 9/1994 | Boenish et al. | | |
| 5,455,030 A | 10/1995 | Ladner et al. | | |
| 5,585,100 A * | 12/1996 | Mond | ................. | A61K 39/385 424/193.1 |
| 5,585,362 A | 12/1996 | Wilson et al. | | |
| 5,817,512 A * | 10/1998 | Morrow | ............... | C07K 14/005 424/199.1 |
| 5,939,598 A | 8/1999 | Kucherlapati et al. | | |
| 6,221,664 B1 | 4/2001 | Wen et al. | | |
| 6,660,842 B1 * | 12/2003 | Sallberg | ........................ | 530/350 |
| 7,078,179 B2 | 7/2006 | Di Colandrea et al. | | |
| 7,247,502 B2 | 7/2007 | Ennifar et al. | | |
| 7,452,541 B2 | 11/2008 | Bachmann et al. | | |
| 7,524,627 B2 | 4/2009 | Corvaia et al. | | |
| 2002/0131953 A1 | 9/2002 | Takashima et al. | | |
| 2007/0026502 A1 * | 2/2007 | Sallberg | ............... | G01N 33/569 435/91.1 |
| 2008/0090225 A1 | 4/2008 | Kirkegaard et al. | | |
| 2008/0118530 A1 | 5/2008 | Kew et al. | | |

(Continued)

FOREIGN PATENT DOCUMENTS

| | | |
|---|---|---|
| EP | 0058481 A1 | 8/1982 |
| EP | 0133988 A2 | 3/1985 |

(Continued)

OTHER PUBLICATIONS

Akiyama et al., "Targeting apoptotic tumor cells to Fc gamma R provides efficient and versatile vaccination against tumors by dendritic cells", *J Immunol 170* (4), 1641-1648 (2003).
Altschul et al., "Basic Local Alignment Search Tool", *J. Mol. Biol. 215*, 403-410, (1990).
Apostolopoulos et al., "Targeting Antigens to Dendritic Cell Receptors for Vaccine Development", *Journal of Drug Delivery*, vol. 2013, 22 pages (2013).
Better et al., "Expression of Engineered Antibodies and Antibody Fragments in Microorganisms", *Methods in Enzymology*, 178, 476-496, Academic Press, Inc. (1989).
Bird et al., "Single Chain Antibody Variable Regions", *TIBTECH*, 9, 132-137 (1991).

(Continued)

*Primary Examiner* — Agnieszka Boesen
(74) *Attorney, Agent, or Firm* — Davis, Brown, Koehn, Shors & Roberts, P.C.; Matthew W. Coryell

(57) ABSTRACT

The present invention provides a process called "Immune Banking" that enhances vaccine efficacy by exploiting existing humoral responses. The process involves tagging new antigens with molecular markers recognized by an existing antibody response. This recognition of the tagged vaccine components enhances adaptive immune responses to the new vaccine.

7 Claims, 7 Drawing Sheets

Specification includes a Sequence Listing.

(56) References Cited

U.S. PATENT DOCUMENTS

| | | |
|---|---|---|
| 2008/0260773 A1 | 10/2008 | Del Giudice et al. |
| 2008/0311135 A1 | 12/2008 | Zheng et al. |
| 2008/0311147 A1 | 12/2008 | Schnell et al. |
| 2009/0081210 A1 | 3/2009 | Evans et al. |
| 2009/0324630 A1 | 12/2009 | Jensen |
| 2010/0145015 A1 | 6/2010 | Galili |
| 2010/0249021 A1 | 9/2010 | Gao et al. |
| 2010/0254945 A1 | 10/2010 | Ge et al. |
| 2012/0195926 A1 | 8/2012 | Bishop et al. |

FOREIGN PATENT DOCUMENTS

| | | |
|---|---|---|
| EP | 0239400 A2 | 9/1987 |
| EP | 0404097 A2 | 12/1990 |
| WO | WO 92/01047 A1 | 1/1992 |
| WO | 9214489 | 2/1992 |
| WO | WO 92/03918 A1 | 3/1992 |
| WO | 92014489 | 9/1992 |
| WO | WO 1992/014489 A1 | 9/1992 |
| WO | WO 92/20791 A1 | 11/1992 |
| WO | WO 93/06213 A1 | 4/1993 |
| WO | WO 93/11161 A1 | 6/1993 |
| WO | WO 93/11236 A1 | 6/1993 |
| WO | WO 93/12227 A1 | 6/1993 |
| WO | WO 93/19172 A1 | 9/1993 |
| WO | WO 94/02602 A1 | 2/1994 |
| WO | WO 94/25585 A1 | 11/1994 |
| WO | WO 95/01438 A1 | 1/1995 |
| WO | WO 95/15388 A1 | 6/1995 |
| WO | WO 96/02576 A1 | 2/1996 |
| WO | WO 96/33735 A1 | 10/1996 |
| WO | WO 96/34096 A1 | 10/1996 |
| WO | 2007052238 | 5/2007 |
| WO | WO 08/147847 A1 | 12/2008 |
| WO | 2011041691 | 4/2011 |
| WO | WO 2011/041691 A1 | 4/2011 |

OTHER PUBLICATIONS

Breckpot et al., "Exploiting dendritic cells for cancer immunotherapy: genetic modification of dendritic cells", *J Gene Med* 6, 1175-1188 (2004).

Brennan et al., "Preparation of Bispecific Antibodies by Chemical Recombination of Monoclonal Immunoglobulin $G_1$ Fragments", *Science* 229, 81 (1985).

Brinkley, "A brief survey of methods for preparing protein conjugates with dyes, haptens and cross-linking reagents", *Bioconjugate Chem.*, 3, 2-13 (1992).

Brodeur et al., "Mouse-Human Myeloma Partners for the Production of Heterohybridomas", Immunology series; vol. 33, *Monoclonal Antibody Production Techniques and Application*, pp. 51-63 (1987).

Bros et al., "A novel plasmid DNA electroporation method allows transfection of murine DC", J Immunol Methods 343, 13-20 (2009).

Carter et al., "High Level *Escherichia coli* Expression and Production of a Bivalent Humanized Antibody Fragment", *Bio/Technology* 10, 163-167 (1992).

Champe et al., "Monoclonal Antibodies That Block the Activity of Leukocyte Function-associated Antigen 1 Recognize Three Discrete Epitopes in the Inserted Doman of CD11a", *J. Biol. Chem.* vol. 270, No. 3, 1388-1394 (1995).

Clackson et al., "Making antibody fragments using phage display libraries", *Nature* 352, 624-628 (1991).

Co et al., "A Humanized Antibody Specific for the Platelet Integrin gpIIb/IIIa", *J. Immunol.*, 152, 2968-2976 (1994).

Cristillo et al., "Preclinical evaluation of cellular immune responses elicited by a polyvalent DNA prime/protein boost HIV-1 vaccine", *Virology* 346, 151-168 (2006).

De St. Groth et al., "Prodcution of Monoclonal Antibodies: Strategy and Tactics", *J. Immunol. Methods*, 35, 1-21 (1980).

Faulkner et al., "Influenza hemagglutinin peptides fused to interferon gamma and encapsulated in liposomes protects mice against influenza infection", *Vaccine*, vol. 21, No. 9-10, 932-939 (2003).

Flinsenberg et al., "Fcγ receptor antigen targeting potentiates cross-presentation by human blood and lymphoid tissue BDCA-3+ dendritic cells", *Blood* 120 (26), 5163-5172 (2012).

Galfre et al., "Rat x rat hybrid myelomas and a monoclonal anti-Fd portion of mouse IgG", *Nature*, 277, 131-133 (1979).

Galfre et al., "Preparation of Monoclonal Antibodies: Strategies and Procedures", *Methods Enzymol.* 73, 3-46 (1981).

Getahun et al., "IgG2a-Mediated Enhancement of Antibody and T Cell Responses and its Relation to Inhibitory and Activating Fcγ Receptors", *The Journal of Immunology*, 172, 5269-5276 (2004).

Getahun et al., "How antibodies act as natural adjuvants", *Immunol Lett.* 104(1-2), 38-45, (2006).

Gosselin et al., "Fc receptor-targeted mucosal vaccination as a novel strategy for the generation of enhanced immunity against mucosal and non-mucosal pathogens", *Arch Immunol Ther Exp* 57 (5), 311-323 (2009).

Gosselin et al., "Fc receptor-targeted vaccines: an adjuvant-independent approach for mucosal vaccination against intracellular and extracellular mucosal pathogens (P4290)", *Journal of Immunology*, 190, 54.14, Abstract, 2 pages (2013).

Granoff et al., "Effect of immunity to the carrier protein on antibody responses to Haemphilus influenza type b conjugate vaccines", *Vaccine*, vol. 11, Supp. 1, S46-S51 (1993).

Green et al., "Antigen-specific human monoclonal antibodies from mice engineered with human Ig heavy and light chain YACs", *Nature Genetics* 7, 13-21 (1994).

Hannum et al., "Germinal Center Initiation, Variable Gene Region Hypermutation, and Mutant B Cell Selection without Detectable Immune Complexes on Follicular Dendritic Cells", *J Exp Med* 192, 931-942 (2000).

Heyman, "Regulation of antibody responses via antibodies, complement, and Fc receptors", *Annu Rev Immunol* 18, 709-737 (2000).

Heyman, "Feedback regulation by IgG antibodies", *Immunol. Lett.* 88 (2), 157-161 (2003).

Hjelm et al., "Antibody-mediated regulation of the immune response", *Scand J Immunol* 64, 177-184 (2006).

Holliger et al., "Diabodies: Small bivalent and bispecific antibody fragments", *Proc. Natl. Acad. Sci. USA* 90, 6444-6448 (1993).

Huang et al., "Specific immune responses induced by a multi-epitope antigen of hepatitis C virus in mice and rabbits", *Chinese Sci. Bull.* 45, 903-908 (2000).

Huston et al., "Protein engineering of antibody binding sites: Recovery of specific activity in an anti-digoxin single-chain Fv analogue produced in *Escherichia coli*", *Proc. Natl. Acad. Sci. USA*, 85, 5879-5883 (1988).

Jones et al., "Replacing the complementarity-determining regions in a human antibody with those from a mouse", *Nature* 321, 522-525 (1986).

Karlin et al., "Applications and statistics for multiple high-scoring segments in molecular sequences", *Proc. Natl. Acad. Sci.* USA, 90, 5873-5877 (1993).

Karlsson et al., "Efficient IgG-mediated suppression of primary antibody responses in Fcγ receptor-deficient mice", *Proc. Natl. Acad. Sci.* vol. 96, 2244-2249 (1999).

Karlsson et al., "IgE-mediated suppression of primary antibody responses in vivo", *Scand J Immunol* 53 (4), 381-385 (2001).

Katz, "Carrier Function in Anti-Hapten Immune Responses: I. Enhancement of Primary and Secondary Anti-Hapten Antibody Responses by Carrier Preimmunization", *Journal of Experimental Medicine*, vol. 132, No. 2, 261-282.

Kearney et al., "A new mouse myeloma cell line that has lost immunoglobulin expression but permits the construction of antibody-secreting hybrid cell lines", *J. Immunol.*, vol. 123, No. 4, 1548-1550 (1979).

Khopade et al., "Surface-Modification of Polyelectrolyte Multilayer-Coated Particles for Biological Applications", *Langmuir* 19, 6219-6225 (2003).

Kohler et al., "Continuous cultures of fused cells secreting antibody of predefined specificity", Nature 256, 495-497, (1975).

(56) References Cited

OTHER PUBLICATIONS

Kohler et al., "Derivation of specific antibody-producing tissue culture and tumor lines by cell fusion", *Eur. J. Immunol.*, 6, 511-519 (1979).
Kozbar et al., "A human hybrid myeloma for production of human monoclonal antibodies", *J. Immunol.* vol. 133, No. 6, 3001-3005 (1984).
Kraus et al., "TNF receptor-associated factor 5 is required for optimal T cell expansion and survival in response to infection", *J Immunol 181*, 7800-7809 (2008).
Kunkel, "Rapid and efficient site-specific mutagenesis without phenotypic selection", *Proc. Natl. Acad. Sci.* USA 82, 488-492 (1985).
Kunkel et al., "Rapid and Efficient Site-Specific Mutagenesis without Phenotypic Selection", *Meth. Enzymol.*, 154, 367-382 (1987).
Kurikka, "Priming with diphtheria-tetanus-pertussis vaccine enhances the response to the Haemophilus influenza type b tetanus conjugate vaccine in infancy", *Vaccine*, vol. 14, No. 13, 1239-1242 (1996).
Lamoyi, "Preparation of F(ab')$_2$ Fragments from Mouse IgG of Various Subclasses", *Methods in Enzymology*, 121, 663-669 (1989).
Langer et al., "Biocompatibility of polymeric delivery systems for macromolecules", *J. Biomed. Mater. Res.* 15, 167-277 (1981).
Langer, "Controlled release of macromolecules", *Chem. Tech.* 12, 98-105 (1982).
Legge et al., "Lymph node dendritic cells control CD8+ T cell responses through regulated FasL expression", *Immunity 23*, 649-659 (2005).
Levine et al., "A B-cell receptor-specific selection step governs immature to mature B cell differentiation", *Proc Natl Acad Sci* USA vol. 97, No. 6 2743-2748 (2000).
Lonberg et al., "Antigen-specific human antibodies from mice comprising four distinct genetic modifications", Nature 368, 856-859 (1994).
Margulies et al., "Somatic Cell Hybridization of Mouse Myeloma Cells", *Cell 8*, 405-415 (1976).
Marks et al. "By-passing Immunization, Human Antibodies from V-gene Libraries Displayed on Phage", *J. Mol. Biol.* 222, 581-597 (1991).
Marks et al., "By-Passing Immunization: Building High Affinity Human Antibodies by Chain Shuffling", *Bio/Technology 10*, 779-783 (1992).
Martin et al., "Transport of Incoming Influenza Virus Nucleocapsids into the Nucleus", *J. Virol.* vol. 65(1), 232-244 (1991).
McCafferty et al. "Phage antibodies: filamentous phage displaying antibody variable domains", *Nature 348*, 552-554 (1990).
McGhee et al., "New Perspectives in Mucosal Immunity with Emphasis on vaccine developments", *Sem. Hematol.*, vol. 30, No. 4, Suppl 4, 2-15 (1993).
Mendez et al., "Functional transplant of megabase human immunoglobulin loci recapitulates human antibody response in mice", *Nature Genetics 15*, 46-156 (1997).
Morimoto et al., "Single-step purification of F(ab')$_2$ fragments of mouse monoclonal antibodies (immunoglobulines Gl) by hydrophobic interaction high performace liquid chromatography using TSKgel Phenyl-5PW", Journal of Biochemical and Biophysical Methods 24, 107-117 (1992).
Morrison et al., "Chimeric human antibody molecules" Mouse antigen-binding domains with human constant region domains, *Proc. Natl. Acad. Sci.* USA 81, 6851-6855, (1984).
Needleman et al., "A General Method Applicable to the Search for Similarities in the Amino Acid Sequence of Two Proteins", *J. Mol. Biol.*, 48, 443 (1970).
Patent Cooperation Treaty, International Searching Authority, Search Report and Written Opinion for PCT/US2012/032190, 17 pages, dated Sep. 21, 2012.
Peeters et al., "Effect of Carrier Priming on Immunogenicity of Saccharide-Protein Conjugate Vaccines", *Infection and Immunity*, vol. 59, No. 10, 3504-3510 (1991).

Pluckthun, "Antibodies from *Escherichia coli*" *The Pharmacology of Monoclonal Antibodies* vol. 113, Chapt. 11, eds. Rosenburg and Moore, Springer Verlag, N.Y., 269-315 (1994).
Pluckthun et al., A., "Expression of Functional Antibody Fv and Fab Fragments in *Escherichia coli*", *Methods in Enzymology*, 178, *Antibodies, Antigens, and Molecular Mimicry*, 476-496 (1989).
Presta, "Antibody Engineering", *Curr. Op. Struct. Biol.* 2, 593-596 (1992).
Rawool et al., "Utilization of Fc Receptors as a Mucosal Vaccine Strategy against an Intracellular Bacterium, *Francisella tularensis*", *Journal of Immunology*, 180, 5548-5557 (2008).
Reichmann et al., "Reshaping human antibodies for therapy", *Nature 332*, 323-329 (1988).
Sato et al., "Reshaping a Human Antibody to Inhibit the Interleukin 6-dependent Tumor Cell Growth", *Cancer Res.* 53, 851-856 (1993).
Shreder, "Synthetic Haptens as Probes of Antibody Response and Immunorecognition", *Methods 20*, 373-379 (2000).
Shulman et al., "A better cell line for making hybridomas secreting specific antibodies", *Nature 276*, 269-270 (1978).
Sidman et al., "Controlled Release of Macromolecules and Pharmaceuticals from Synthetic Polypeptides Based on Glutamic Acid", *Biopolymers 22*, 547-556 (1983).
Stunz et al., "Expression of the cytoplasmic tail of LMP1 in mice induces hyperactivation of B lymphocytes and disordered lymphoid architecture", *Immunity 21*, 255-266 (2004).
Sudowe et al., "Transcriptional targeting of dendritic cells in gene gun-mediated DNA immunization favors the induction of type 1 immune responses", *Mol Ther* vol. 8 No. 4, 567-575 (2003).
Takai et al., "FcR gamma chain deletion results in pleiotrophic effector cell defects", *Cell 76*, 519-529 (1994).
Trevisan et al., "Compliance with hepatitis B virus vaccine: a matter of force?", Am J Infect Control vol. 34, No. 7, 465-466 (2006).
Trowbridge, "Interspecies Spleen-Myeloma Hybrid Producing Monoclonal Antibodies Against Mouse Lymphocyte Surface Glycoprotein, T200" *J. Exp. Med.* 148, 313-323 (1978).
Unkeless, "Characterization of a Monoclonal Antibody Directed Against Mouse Macrophage and Lymphocyte Fc Receptors", *J. Exp. Med.*, vol. 150, No. 3, 580-596 (1979).
Wang et al., "Multi-Component One-Pot Synthesis of the Tumor-Associated Carbohydrate Antigen Globo-H Based on Preactivation of Thioglycosyl Donors", *J. Oar . Chem.* 72 64-9-6420 (2007).
Waterhouse et al., "Combinatorial infection and in vivo recombination: a strategy for making large phage antibody repertoires", *Nucleic Acids Res.* vol. 21, No. 9, 2265-2266 (1993).
Wernersson et al., "IgG-mediated enhancement of antibody responses is low in Fc receptor gamma chain-deficient mice and increased in Fc gamma RII-deficient mice", *J Immunol 163*, 618-622 (1999).
Wernersson et al., "Immune complex-mediated enhancement of antibody responses without induction of delayed-type hypersensitivity", *Scand J. Immunol*, 52(6), 563-569, (2000).
Xie et al., "Tumor necrosis factor receptor-associated factor 3 is a critical regulator of B cell homeostasis in secondary lymphoid organs", *Immunity 27*, 253-267 (2007).
Yada et al., "Accelerated antigen presentation and elicitation of humoral response in vivo by FcγRIIB- and FcγRI/III-mediated immune complex uptake", *Cellular Immunology 225*, 21-32 (2003).
Yelton et al., "Fusion of Mouse Myeloma and Spleen Cells", *Current Topics in Microbiology and Immunology*, 81, 1-7 (1978).
Zheng et al., "Correction of age-associated deficiency in germinal center response by immunization with immune complexes", *Clinical Immunology*, 124, 131-137 (2007).
Zheng et al., "Rectification of age-associated deficiency in cytotoxic T cell response to influenza A virus by immunization with immune complexes", *The Journal of Immunology*, 179, 6153-6159 (2007).
Kubota-Koketsli et al., "Broad neutralizing human monoclonal antibodies against influenza virus from vaccinated healthy donors", Sep. 11, 2009, pp. 180-185, vol. 387, No. 1, Publisher: Biochemical and Biophysical Research Communications.
Burke et al., "A Cassette Vector for the Construction of Antigen Chimaeras of Poliovirus", Sep. 1, 1989, pp. 2475-2479, vol. 70, No. 9.

(56) References Cited

OTHER PUBLICATIONS

Rao et al., "Comparative efficacy of hemagglutinin nucleoprotein and matrix 2 protein gene-based vaccination against H5N1 influenza in mouse and ferret", Mar. 23, 2010, pp. 1-11, vol. 5, No. 3.
Delpeyroux et al., "Construction and characterization of hybrid hepatits b antigen particles carrying a poliovirus immunogen", Aug. 1, 1988, pp. 1065-1073, vol. 70, No. 8.
Yewdell et al., "Influenza a virus nucleoprotein is a major target antigen for cross-reactive anti-influenza a virus cytotoxic t lymphocytes", Mar. 1, 1985, pp. 1785-1789, vol. 82, No. 6.
Samuelson et al., "Molecular Basis for Serological Cross-Reactivity between Enteroviruses", May 1, 1994, pp. 336-341, vol. 1, No. 3, Publisher: Division of Clinical Virology.
Kurikka et al., "Priming with diphtheria tatanus pertussis vaccine enhances the response to the Haemophilus influenzae type b tatanus conjugate vaccine in infancy", Sep. 1, 1996, pp. 1239-1242, vol. 14, No. 13.
Granoff D. M., "Effect of immunity to the carrier protein on antibody responses to haemophilus influenza tybe b conjugate vaccines", "Vaccine", Jan. 1, 1993, pp. S46-S51, vol. 11, Publisher: Elsevier.
U.S. Appl. No. 13/499,891, 2012-0195926.

* cited by examiner

Ag1:KLH-TNP conjugate or controls (PBS alone, KLH, KLH-NP, or BSA-TNP)   ● Blood collection to test for Ag1 and hapten-specific antibodies Figure 5
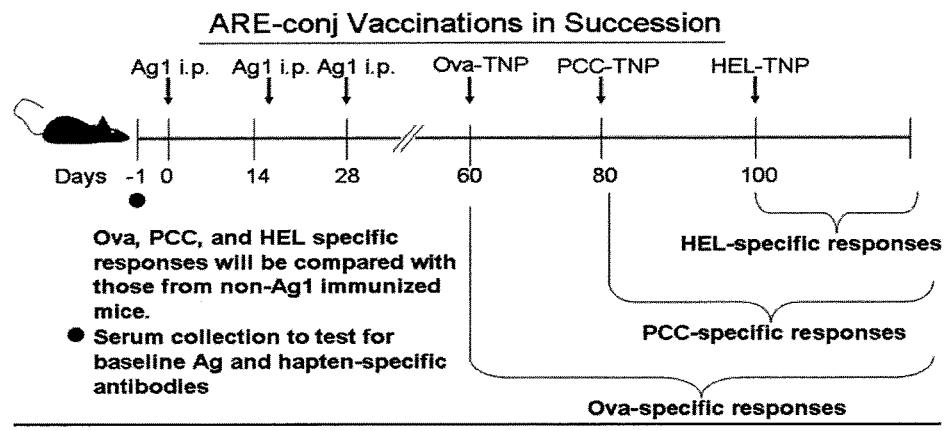
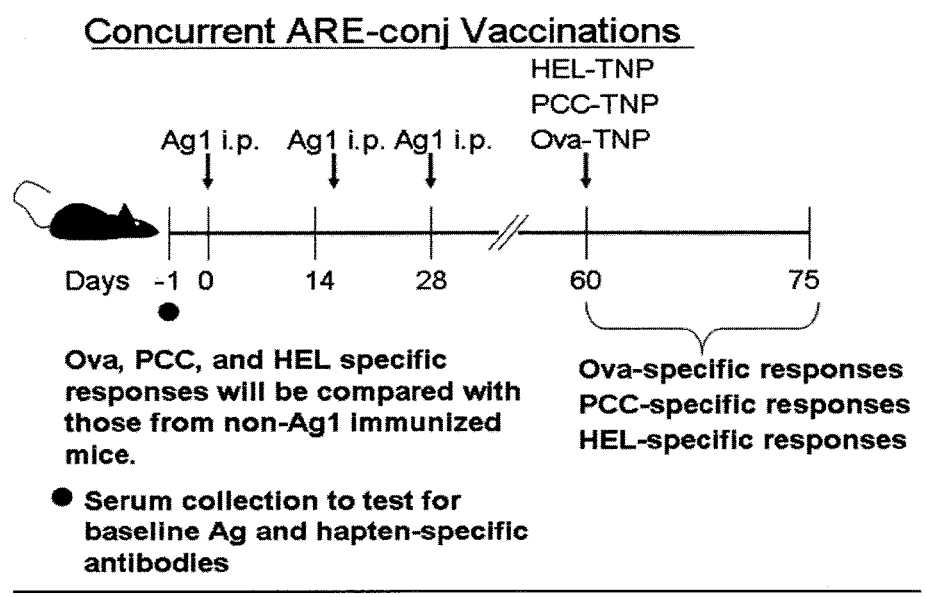

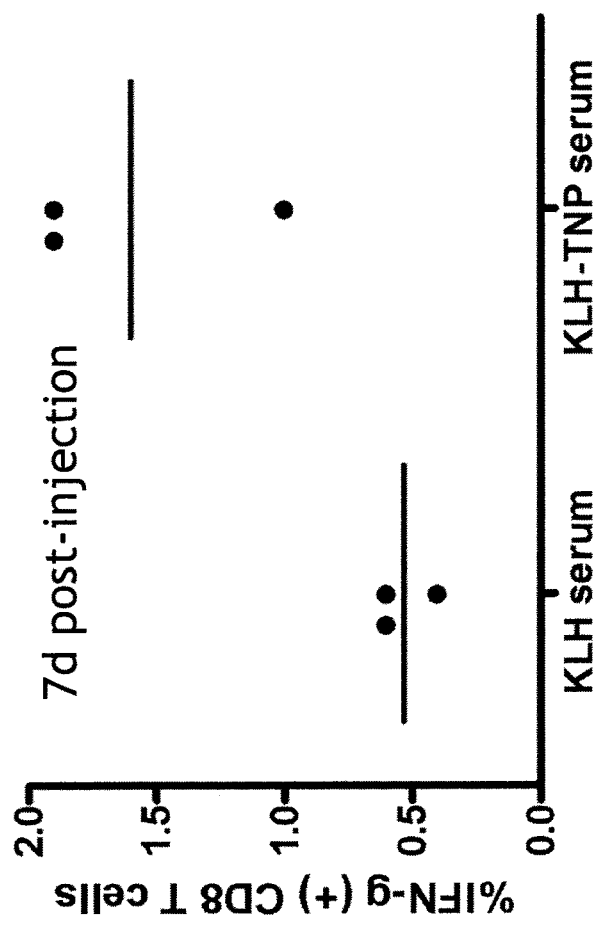
Fig. 7. Role of soluble Ag-specific immunoglobulin in enhanced responses Fig. 8. Determination of the efficacy of ARE modified peptide vaccines

SEQUENCE LISTING

```
<160> NUMBER OF SEQ ID NOS: 14

<210> SEQ ID NO 1
<211> LENGTH: 11
<212> TYPE: PRT
<213> ORGANISM: Human poliovirus 1

<400> SEQUENCE: 1

Ile Pro Ala Leu Thr Ala Val Glu Thr Gly Ala
1               5                   10

<210> SEQ ID NO 2
<211> LENGTH: 18
<212> TYPE: PRT
<213> ORGANISM: Human poliovirus 1

<400> SEQUENCE: 2

Ala His Ser Lys Glu Ile Pro Ala Leu Thr Ala Val Glu Thr Gly Ala
1               5                   10                  15

Thr Ala

<210> SEQ ID NO 3
<211> LENGTH: 10
<212> TYPE: PRT
<213> ORGANISM: Human poliovirus 1

<400> SEQUENCE: 3

Ala Leu Thr Ala Val Glu Thr Gly Ala Thr
1               5                   10

<210> SEQ ID NO 4
<211> LENGTH: 9
<212> TYPE: PRT
<213> ORGANISM: Unknown
<220> FEATURE:
<223> OTHER INFORMATION: Description of Unknown: Influ-NP MHC
      class I epitope peptide

<400> SEQUENCE: 4

Ala Ser Asn Glu Asn Met Glu Thr Met
1               5

<210> SEQ ID NO 5
<211> LENGTH: 12
<212> TYPE: PRT
<213> ORGANISM: Unknown
<220> FEATURE:
<223> OTHER INFORMATION: Description of Unknown: HBsAg MHC
      class I epitope peptide

<400> SEQUENCE: 5

Ile Pro Gln Ser Leu Asp Ser Trp Trp Thr Ser Leu
1               5                   10

<210> SEQ ID NO 6
<211> LENGTH: 17
<212> TYPE: PRT
<213> ORGANISM: Unknown
<220> FEATURE:
<223> OTHER INFORMATION: Description of Unknown: Ovalbumin MHC
      class II epitope peptide

<400> SEQUENCE: 6

Ile Ser Gln Ala Val His Ala Ala His Ala Glu Ile Asn Glu Ala Gly
1               5                   10                  15
```

Arg

```
<210> SEQ ID NO 7
<211> LENGTH: 15
<212> TYPE: PRT
<213> ORGANISM: Unknown
<220> FEATURE:
<223> OTHER INFORMATION: Description of Unknown: Influ-NP MHC
      class II epitope peptide

<400> SEQUENCE: 7

Gln Val Tyr Ser Leu Ile Arg Pro Asn Glu Asn Pro Ala His Lys
1               5                   10                  15

<210> SEQ ID NO 8
<211> LENGTH: 15
<212> TYPE: PRT
<213> ORGANISM: Unknown
<220> FEATURE:
<223> OTHER INFORMATION: Description of Unknown: Influ-NP MHC
      class II epitope peptide

<400> SEQUENCE: 8

Arg Ser Ala Leu Ile Leu Arg Gly Ser Val Ala His Lys Ser Cys
1               5                   10                  15

<210> SEQ ID NO 9
<211> LENGTH: 24
<212> TYPE: PRT
<213> ORGANISM: Unknown
<220> FEATURE:
<223> OTHER INFORMATION: Description of Unknown: HBsAg MHC
      class II epitope peptide

<400> SEQUENCE: 9

Cys Thr Thr Pro Ala Gln Gly Asn Ser Met Phe Pro Ser Cys Cys Cys
1               5                   10                  15

Thr Lys Pro Thr Asp Gly Asn Cys
            20

<210> SEQ ID NO 10
<211> LENGTH: 4
<212> TYPE: PRT
<213> ORGANISM: Unknown
<220> FEATURE:
<223> OTHER INFORMATION: Description of Unknown: HBsAg MHC
      variant epitope peptide

<400> SEQUENCE: 10

Arg Ala Gly Gly
1

<210> SEQ ID NO 11
<211> LENGTH: 8
<212> TYPE: PRT
<213> ORGANISM: Unknown
<220> FEATURE:
<223> OTHER INFORMATION: Description of Unknown: Ovalbumin MHC
      class I epitope peptide

<400> SEQUENCE: 11

Ser Ile Ile Asn Phe Glu Lys Leu
1               5

<210> SEQ ID NO 12
<211> LENGTH: 498
<212> TYPE: PRT
```

<213> ORGANISM: Influenza A virus

<400> SEQUENCE: 12

```
Met Ala Ser Gln Gly Thr Lys Arg Ser Tyr Glu G

```
Ala Ser Ala Gly Gln Ile Ser Val Gln Pro Thr Phe Ser Val Gln Arg
            405                 410                 415

Asn Leu Pro Phe Glu Arg Ala Thr Ile Met Ala Ala Phe Thr Gly Asn
            420                 425                 430

Thr Glu Gly Arg Thr Ser Asp Met Arg Thr Glu Ile Ile Arg Met Met
            435                 440                 445

Glu Ser Ala Arg Pro Glu Asp Val Ser Phe Gln Gly Arg Gly Val Phe
            450                 455                 460

Glu Leu Ser Asp Glu Lys Ala Thr Asn Pro Ile Val Pro Ser Phe Asp
465                 470                 475                 480

Met Asn Asn Glu Gly Ser Tyr Phe Phe Gly Asp Asn Ala Glu Glu Tyr
                485                 490                 495

Asp Asn

<210> SEQ ID NO 13
<211> LENGTH: 498
<212> TYPE: PRT
<213> ORGANISM: Influenza A virus

<400> SEQUENCE: 13

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270
```

```
Lys Ser Cys Leu Pro Ala Cys Val Tyr Gly Pro Ala Val Ala Ser Gly
            275                 280                 285

Tyr Asp Phe Glu Arg Glu Gly Tyr Ser Leu Val Gly Ile Asp Pro Phe
            290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
            325                 330                 335

Ala Phe Glu Asp Leu Arg Val Leu Ser Phe Ile Lys Gly Thr Lys Val
            340                 345                 350

Leu Pro Arg Gly Lys Leu Ser Thr Arg Gly Val Gln Ile Ala Ser Asn
            355                 360                 365

Glu Asn Met Glu Thr Met Glu Ser Ser Thr Leu Glu Leu Arg Ser Arg
370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
            405                 410                 415

Asn Leu Pro Phe Asp Arg Thr Thr Ile Met Ala Ala Phe Asn Gly Asn
            420                 425                 430

Thr Glu Gly Arg Thr Ser Asp Met Arg Thr Glu Ile Ile Arg Met Met
            435                 440                 445

Glu Ser Ala Arg Pro Glu Asp Val Ser Phe Gln Gly Arg Gly Val Phe
            450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
            485                 490                 495

Asp Asn

<210> SEQ ID NO 14
<211> LENGTH: 565
<212> TYPE: PRT
<213> ORGANISM: Influenza A virus

<400> SEQUENCE: 14

Met Lys Ala Asn Leu Leu Val Leu Leu Cys Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140
```

```
Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
            165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Leu Tyr
            195                 200                 205

Gln Asn Glu Asn Ala Tyr Val Ser Val Val Thr Ser Asn Tyr Asn Arg
210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
            245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
            275                 280                 285

His Glu Cys Asn Thr Lys Cys Gln Thr Pro Leu Gly Ala Ile Asn Ser
            290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Ile Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
            355                 360                 365

His Gln Asn Glu Gln Gly Ser Gly Tyr Ala Ala Asp Gln Lys Ser Thr
            370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
            485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
            515                 520                 525

Ile Leu Ala Ile Tyr Ser Thr Val Ala Ser Ser Leu Val Leu Leu Val
530                 535                 540
```

```
Ser Leu Gly Ala Ile Ser Phe Trp Met Cys Ser Asn Gly Ser Leu Gln
545                 550                 555                 560

Cys Arg Ile Cys Ile
                565
```

METHODS OF IMPROVING VACCINE IMMUNOGENICITY

PRIORITY OF INVENTION

This application is a US National Phase Application of PCT/US2012/032190, filed on Apr. 4, 2012, which claims priority to U.S. Provisional Application No. 61/471,553 that was filed on Apr. 4, 2011. The entire content of this provisional application is hereby incorporated herein by reference.

STATEMENT OF GOVERNMENT RIGHTS

This invention was made with government support under AI057160-06 awarded by The National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 20, 2012, is named 17023114W.txt and is 16,382 bytes in size.

BACKGROUND OF THE INVENTION

The immune system is quite complex and includes many different pathways for an organism to fight infectious pathogens and cancer cells. In general, the immune system is viewed as being able to mount a humoral immune response (HIR) and/or a cell-mediated immune response (CMI). The HIR involves the production and secretion of antibodies produced in the cells of the B lymphocyte lineage (B-cells). Secreted antibodies bind to antigens on the surfaces of invading microbes (such as viruses or bacteria). The antibody-bound antigens are then destroyed by various cells in the immune system. Humoral immunity also refers to antibody production and the accessory processes that accompany it. It also refers to the effector functions of antibody, which include pathogen and toxin neutralization, classical complement activation, and opsonin promotion of phagocytosis and pathogen elimination.

The second type of immune response is cell-mediated immunity (CMI). CMI is an immune response that does not involve antibodies or complement but instead involves the activation of various immune cells, such as macrophages, natural killer cells (NK), antigen-specific cytotoxic T-lymphocytes, and the release of various cytokines in response to an antigen. Cellular immunity can protect the body by activating antigen-specific T-lymphocytes. These cells induce apoptosis in body cells displaying epitopes of foreign antigen on their surface, such as virus-infected cells, cells infected with intracellular bacteria, and cancer cells displaying tumor antigens. T cells activate macrophages and natural killer cells, enabling them to destroy intracellular pathogens, and stimulating cells to secrete a variety of cytokines that influence the function of other cells involved in adaptive and innate immune responses. Cell-mediated immunity is directed primarily at microbes that survive in phagocytes and microbes that infect non-phagocytic cells. It is most effective in removing virus-infected cells, but also participates in defending against fungi, protozoans, cancers, and intracellular bacteria.

Traditionally, as defined by the World Health Organization, a vaccine is any preparation intended to produce immunity to a disease by stimulating the production of antibodies. Vaccines include, for example, suspensions of killed or attenuated microorganisms, or products or derivatives of microorganisms. The most common method of administering vaccines is by inoculation, but some are given by mouth or nasal spray.

Present vaccine technologies rely on large doses of antigen and/or re-vaccinations (booster shots) and do not confer protection against all infectious agents. Therefore, a need exists for new vaccines to confer protection against infectious agents for which there currently are no effective vaccines. There is also a need for new vaccines that are safer to administer, are less expensive to produce, and/or do not require booster shots. The elimination of booster shots would increase immunization compliance. Finally, some human populations, such as the elderly, make overall weaker responses to vaccination, and more effective vaccines could better protect this growing category of vaccine recipients.

SUMMARY OF THE INVENTION

In certain embodiments, the present invention provides a compound comprising at least one antigen covalently bound to an antibody-recognition epitope (ARE, also called "antibody recognition elements" or "antibody reactive epitopes"). In certain embodiments, the present invention provides a VP-1 epitope of polio of about 11-28 amino acids in length comprising IPALTAVETGA (SEQ ID NO: 1). In certain embodiments, the epitope is about 18-28 amino acids in length and comprises IPALTAVETGA (SEQ ID NO: 1). In certain embodiments, the epitope consists essentially of, or consists of, IPALTAVETGA (SEQ ID NO: 1).

In certain embodiments the epitope is about 11-28 amino acids in length and comprises ALTAVETGAT (SEQ ID NO: 3). In certain embodiments, the present invention provides a VP-1 epitope of polio of about 18-28 amino acids in length comprising ALTAVETGAT (SEQ ID NO: 3). In certain embodiments the epitope consists essentially of, or consists of, ALTAVETGAT (SEQ ID NO: 3). In certain embodiments the epitope is 18-28 amino acids in length and comprises, consists essentially of, or consists of AHSKEIPALTAVETGATA (SEQ ID NO: 2).

In certain embodiments, the present invention provides a compound comprising at least one antigen covalently bound to an antibody-recognition epitope (ARE), wherein the ARE is a VP-1 epitope described above. In certain embodiments, the antigen is bound to the ARE by means of an alpha-Gal linkage. In certain embodiments, the antigen is bound to the ARE by means of linker molecule. In certain embodiments, the linker molecule is formaldehyde, gluteraldehyde, MBS (m-Maleimidobenzoyl-N-hydroxysuccinimide ester) and/or Sulfo-MBS. In certain embodiments, the antigen is an infectious agent antigen. In certain embodiments, the infectious agent is a bacterial, fungal, parasitic, viral, or prion agent. In certain embodiments, the infectious agent is a bacterial agent or a viral agent. In certain embodiments, the antigen is a cancer antigen.

In certain embodiments, the antigen is further conjugated to an antibody to form an antibody:antigen complex. As used herein, the term "antibody" includes scFv, humanized, fully human or chimeric antibodies, single-chain antibodies, diabodies, and antigen-binding fragments of antibodies (e.g., Fab fragments). In certain embodiments, the antibody is a human antibody or a humanized antibody. In certain embodiments, the antibody is a single-chain Fv or an scFv fragment.

In certain embodiments, the hapten is operably linked to the antigen to form a haptenated antigen. In certain embodiments, the hapten is operably linked to a further antigen.

In certain embodiments, the present invention provides a complex comprising a compound comprising at least one antigen covalently conjugated to an antibody-recognition epitope (ARE) operably linked to a conjugation molecule. In certain embodiments, the conjugation molecule is a peptide, a nucleic acid, or a polysaccharide that is not the antigen or ARE.

In certain embodiments, the present invention provides a composition comprising a compound comprising at least one antigen conjugated to an antibody-recognition epitope (ARE) and a physiologically-acceptable, non-toxic vehicle. In certain embodiments, the composition, further comprises an adjuvant.

In certain embodiments, the present invention provides a method of eliciting an immune response in a pre-immunized animal comprising introducing into the animal the composition described above. In certain embodiments, the introduction of the composition occurs at least 15 days after the pre-immunization. In certain embodiments, the method further comprises introducing a second composition described above. In certain embodiments, the method further comprises introducing a repeat dose of the composition. In certain embodiments, the animal is a human.

In certain embodiments, the present invention provides a method of generating antibodies specific for an antigen, comprising introducing into the animal the composition or complex described above. In certain embodiments, the method further comprises introducing a second dose of the composition or the complex into the animal.

In certain embodiments, the present invention provides a method of treating cancer, comprising administering to a patient the composition or the complex described above.

In certain embodiments, the present invention provides a method of preventing or treating an infection or infectious disease comprising administering to a patient the composition or the complex described above.

In certain embodiments, the present invention provides a compound comprising at least one antigen conjugated to an antibody-recognition epitope (ARE) for use in the prophylactic or therapeutic treatment of an infectious agent or cancer.

In certain embodiments, the present invention provides a compound comprising at least one antigen conjugated to an antibody-recognition epitope (ARE) for the manufacture of a medicament useful for the treatment of an infectious agent or cancer in a mammal.

The present invention provides a compound comprising at least one antigen covalently bound to an antibody-recognition epitope (ARE), wherein the antigen is Nucleocapsid Protein (NP) from Influenza A H5N1 (A/Indonesia/5/2005 (H5N1)) Genebank protein accession number #ABI36003 and the ARE is VP-1 epitope of polio of about 11-28 amino acids in length comprising IPALTAVETGA (SEQ ID NO: 1), and wherein the ARE is covalently bound directly to the NP.

In certain embodiments, the present invention provides a nucleic acid encoding the VP-1 epitope described above operably linked to nucleic acid encoding an antigen.

In certain embodiments, the present invention provides an expression cassette comprising a promoter contiguously linked to a nucleic acid encoding the VP-1 epitope described above operably linked to nucleic acid encoding an antigen. In certain embodiments, the promoter is a tissue-specific promoter. In certain embodiments, the promoter is an inducible promoter. In certain embodiments, the promoter is a CMV, RSV, EFa-1, or T7 promoter.

In certain embodiments, the present invention provides a vector comprising the expression cassette described above. In certain embodiments, the vector is an adeno-associated virus (AAV) vector.

BRIEF DESCRIPTION OF THE FIGURES

FIG. 5 shows timelines for the ARE-conj vaccinations in succession and for concurrent ARE-conj vaccinations.

FIG. 7 shows the role of soluble Ag-specific immunoglobulin in enhanced responses. Serum from KLH or KLH-TNP immunized mice was incubated with TNP conjugated ovalbumin. The resulting mixtures containing ovalbumin-TNP plus mouse serum or ovalbumin-TNP:antibody complexes were injected into naïve mice (3 per group). Seven days post ovalbumin injection the percent of ova-specific splenic CD8 T cells was determined by intracellular cytokine staining. Note that the injection of immune complexes using TNP as an ARE enhances the cellular response to the vaccine.

FIG. 8 shows the determination of the efficacy of ARE modified peptide vaccines. Mice with ARE specific antibodies show less morbidity after vaccination and challenge with Influenza. Mice were either mock vaccinated (alum w/PBS) or immunized against Hepatitis B using the human vaccine (HBsAg—in alum). Upon sero-conversion to HBsAg in the test group, both groups of mice received a Hepatitis ARE tagged influenza nucleoprotein vaccine (HepPep—covalently linked to the nucleoprotein—NP—of influenza). Both groups were then challenged with virulent influenza and morbidity determined by weightloss. The HepPep-ARE tagged vaccine group shows less morbidity than the control group.

DETAILED DESCRIPTION OF THE INVENTION

Figure 1:
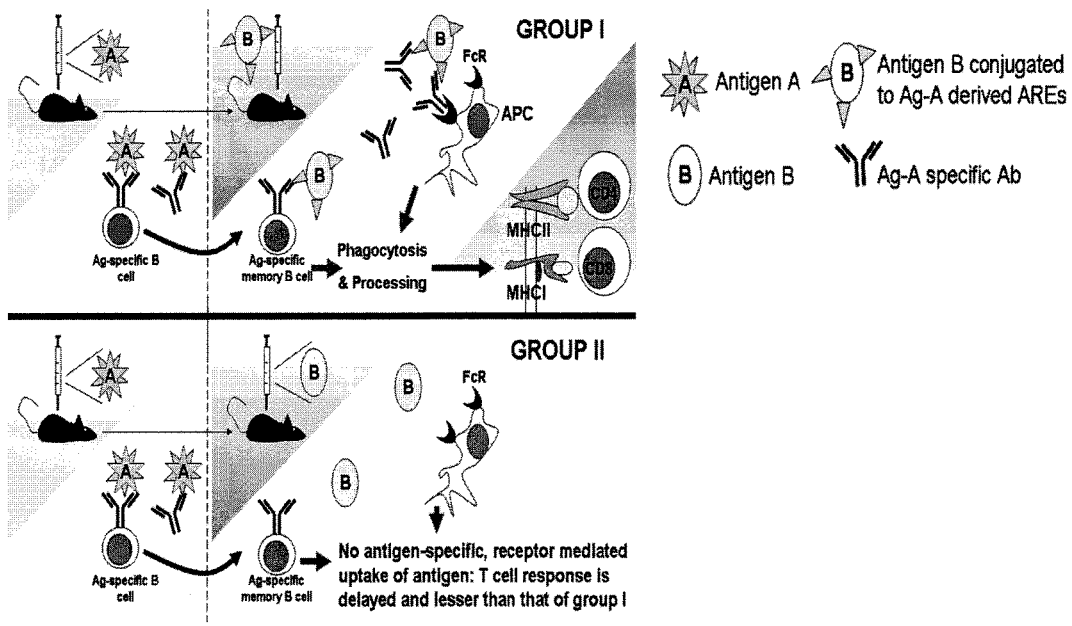
FIG. 1 Proposed mechanism(s) of enhanced cellular immune response to Ab-recognition element (ARE) conjugated Ags. Mouse groups I and II have humoral response to AgA. Group I is then immunized with AgB conjugated to AgA derived AREs. In contrast, Group II is immunized against a non-conjugated AgB. AgA specific humoral response recognizing ARE conjugated AgB enhance the B-specific adaptive immune response of Group I over that of Group II.

The development of technologies to increase the immunogenicity of subunit vaccines is of major interest to health professionals, military personnel, and the general public. The ability to increase an antigen's immunogenicity improves current vaccines and enhances the development of new vaccines, to reduce infection related morbidity and mortality. In addition to combating infectious diseases, advances in vaccine development benefits cancer patients and suffers of chemical dependence (e.g., vaccination against active chemicals such as cocaine) through immunotherapeutics and immunologic intervention respectively.

Successful immunization results in activation of adaptive immune cells including B lymphocytes (also called "B cells"). B cell activation induces clonal expansion and differentiation into long lived Ab producing cells (plasma cells) and memory B cells. Thus immunized individuals express soluble Abs and maintain memory B cells, each able to recognize particular Ags contained within the original vaccine.

In certain embodiments, the present invention provides a process called "Immune Banking" that enhances vaccine efficacy by exploiting existing humoral responses. The Immune Banking process involves tagging new antigens with molecular markers that are already recognized by an existing antibody response in an individual. This recognition of the tagged vaccine components enhances adaptive immune responses to the new vaccine. Previous vaccine technologies relied on large doses of antigen and/or re-vaccinations (booster shots) and did not confer protection against all infectious agents. Because the Immune Banking process is able to enhance the efficacy of vaccines, it can be used to lower dose requirements for current vaccines, reducing cost of manufacture, and reduce need for booster shots (which would increase immunization compliance). The Immune Banking process also enables the creation of new vaccines to combat emerging infectious agents and cancer for which vaccines do not yet exist. This process also enhances the production of monoclonal and polyclonal antibodies for research uses or clinical treatments. The Immune Banking technology is therefore of great interest to producers of vaccines for both human and animals, biotechnology companies that produce polyclonal and monoclonal antibodies for experimental research, and pharmaceutical companies that produce monoclonal antibodies for treatment of disease.

In certain embodiments, the present invention expands the efficacy of vaccine response, and thus the number of people that respond to a particular vaccine. It also increases the effectiveness of vaccines in newborns. The use of this process overcomes multiple problems in current uses of vaccines including the requirement for multiple vaccinations or "booster shots," need for large dose of vaccine components, inability to vaccinate newborns, difficulty in producing effective vaccines that protect against particular infectious agents, and challenges in preparing vaccines that protect against cancer. Multiple studies have suggested that increasing the efficacy of vaccines through targeting or directed antigens (Ag) to immune cells would help solve these problems. Targeting of antigens to immune cells has been accomplished in laboratory settings by conjugation of Ag with cell-specific ligands or cell-specific antibodies, but the large scale production and development of such vaccines is cost preventative and faces considerable technological obstacles. A simple, effective, cost efficient way to target vaccines antigens to antigen presenting cells (APCs) is therefore paramount. The Immune Banking process achieves this goal by utilizing pre-existing humoral immune response to target or direct vaccine antigens to immune cells, therefore enhancing the immune response to the vaccine.

In certain embodiments of the present invention, an animal (e.g., human) is pre-immunized against a known antigen to generate an initial immune response (i.e., a vaccine is administered, and the animal's immune system mounts an immune response). The pre-immunized animal is then administered a compound comprising at least one antigen conjugated to an antibody-recognition epitope (ARE). The Immune Banking builds on the fact that both animals and humans are routinely subjected to vaccinations with known antigens. In certain embodiments, the Immune Banking vaccines are modified with haptenated antigens, and in certain situations, the Immune Banking vaccines have additional antigens conjugated to them. In certain embodiments, the ARE is VP-1 epitope of polio of about 11-28 amino acids in length comprising IPALTAVETGA (SEQ ID NO: 1). In certain embodiments, the ARE is conjugated to the antigen by means of an alpha-Gal linkage.

Improvement of Vaccine Immunogenicity by Exploiting Pre-Existing Humoral Responses Increasing vaccine immunogenicity improves currently available vaccines and enhances development of new vaccines to reduce infection related morbidity and mortality. Vaccines targeted to antigen-presenting cells (APCs) by conjugation of Ag with APC-specific ligands or Abs display increased immunogenicity. However, the large scale production and development of such vaccines faces cost and technological obstacles. A simple, effective, cost efficient way to target vaccine Ags to APCs is lacking. Successful immunization results in B cell activation, which induces clonal expansion and differentiation into long lived Ab producing plasma and memory B cells. Thus, immunized individuals have soluble Abs and memory B cells, each able to recognize Ags from the original vaccine. The present inventors utilize AREs from one immunization to modify new Ags, thus targeting them to APCs by exploiting existing B memory responses. Specific Ag targeting to APCs uses an existing humoral immune response, and improves immunogenicity of a vaccine. This results in both increased vaccine efficacy and a reduction in the need for repeated immunizations.

Regulation of new Ab responses by pre-existing Abs, a phenomenon known as Ab feedback regulation, was originally described in 1892 by Emil von Berhing (Hjelm, F., et al. 2006. *Scand J Immunol* 64:177-184). Depending on the experimental model, the regulation of new Ab responses can be positive (enhancement) or negative (suppressive) (Heyman, B. 2000. *Annu Rev Immunol* 18:709-737). While not completely understood, the mechanisms of enhancement are thought to be dependent upon FcR mediated uptake of Ab:Ag complexes followed by presentation of Ag to CD4 T cells by APCs. These T cells can then provide "help" to new Ag-specific B cells thereby enhancing Ab responses (Heyman, B. 2000. *Annu Rev Immunol* 18:709-737; Getahun, A., and B. Heyman. 2006. *Immunol Lett* 104:38-45). Interestingly, while discussed over 100 years ago and believed to involve T lymphocytes, the effect of Ab feedback regulation on CD4 and CD8 T cell responses has not been determined. The experiments outlined herein evaluate the effects of pre-existing humoral responses on generating T cell responses to new Ag, and potential usefulness as a new immunization enhancement strategy.

FIG. 1 provides the proposed mechanism(s) of enhanced cellular immune response to ARE conjugated Ags. Mouse groups I and II have humoral responses to AgA. Group I is immunized with AgB conjugated to Ag-A derived AREs. Group II is immunized against a non-conjugated Ag-B. Ag-A specific humoral responses recognizing ARE-conjugated AgB enhance the lymphocyte-specific adaptive immune response of Group I over that of Group II.

Figure 2:
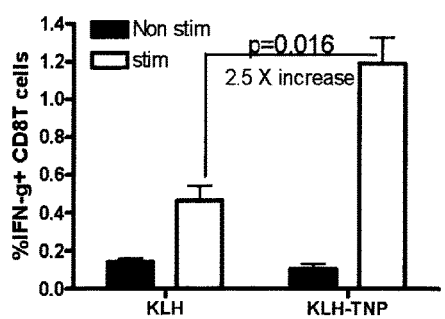
FIG. 2 shows memory CD8 T cell responses.

Table 1 and FIG. 2 show that pre-existing humoral responses to AREs enhanced CD8 T cell responses to ARE-conjugated, novel immunogens.

TABLE 1

|  |  | Primary immunization | |
| --- | --- | --- | --- |
|  |  | KLH | KLH-TNP |
| Secondary Immunization | Ova | None detected | None detected |
|  | Ova-TNP | None detected | Positive Resp |

Role of Pre-Existing Ab Responses in Enhancing Adaptive Immune Response to Novel Ags.

Figure 3:
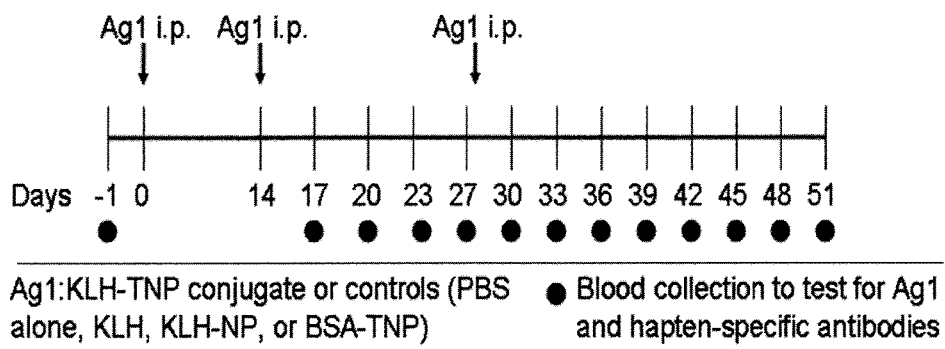
FIG. 3 shows a timeline for when mice are injected with antigen and the days on which blood is collected to test for Ag1 and hapten-specific antibodies.

First, the kinetics of humoral immunity-enhanced T and B cell response are measured. Durable Ag-specific Ab, a measure of vaccine efficacy, results from B cell activation, which leads to generation of long lived Ab producers. Abs provide immune protection in part through opsonization of Ag that facilitates its phagocytosis by immune cells expressing FcRs. Internalized Ag is processed for presentation to T lymphocytes. To quantify the primary response of nave B cells to vaccination, groups of 5 C57Bl/6 mice are injected with TNP-KLH or control Ags (KLH, KLH-NP, BSA-TNP). On day-0 sera is harvested, followed by i.p. immunizations of conjugated or non-haptenated Ags—KLH, KLH-NP, KLH-TNP, BSA-TNP or PBS alone, and a booster immunization on day-14. Sera is collected every three days starting on day-14 and tested, together with preimmune sera, for hapten and carrier specific IgM and IgG (see "General Methods" below). If Ag-specific Abs are not produced after the second immunization, a third Ag injection is given on day-28, again followed by Ag specific Ab measurement in serum every three days (see FIG. 3).

FIG. 2 indicates that T cell responses to new Ags are enhanced when recognized by a pre-existing Ab response (FIG. 1 model). Kinetics and phenotype of enhanced immune responses are compared to those of mice receiving control immunizations. To compare both peak levels of an Ag-specific response and kinetics of humoral-enhanced vs. non-enhanced responses, mice preimmunized with KLH-TNP or control Ags receive ova-TNP i.p. Sera is collected every second day post ova-immunization to evaluate ova-specific Abs (ELISA) and monitor serum cytokines (cytokine multiplex). Because the level of circulating Ag-specific T cells is relatively low after i.p. immunization, the draining tracheobronchial (TB) LN is isolated from 3 mice/group/time and used to evaluate T lymphocyte responses. LN cells are cultured with or without CD4 and CD8 immunodominant peptides (Table 2, see "General Methods" below) for 6 and 24 h. Cells incubated for 6 h are analyzed by flow cytometry, for lineage specific markers (CD4 and CD8) and intracellular IFN-γ, indicative of T lymphocyte responses. Supernatants from 24 h samples are analyzed for multiple cytokines using Luminex® multiplex.

The minimal time needed between unique ARE immunizations and exposure to novel Ag to induce humoral enhanced responses is determined. Using the above model, immunizations with Ova-TNP begin on day-1 after TNP-specific Abs are found in sera of KLH-TNP immunized mice. Preimmune mice are divided into groups based on time of Ova-TNP injections, every 3 d starting at day-15, until peak anti-TNP Ab responses. By determining the minimal time between hapten-booster and second Ag injection necessary to observe the enhanced response, optimal vaccination strategies are developed.

Role of Soluble Ag-Specific Immunoglobulin in Enhanced Responses

The contribution of the humoral response to a T cell response is not clearly understood. An active humoral response to an Ag enhances a CTL response to a new Ag conjugated to the original immunogen (FIG. 2). It is likely that this enhanced T cell response is due to increased Ag uptake through Ig dependent mechanisms: 1) Ig:Ag complex uptake via FcR on APCs (DCs and my) and 2) Ag uptake by memory B cells specific for the original Ag.

Figure 4:
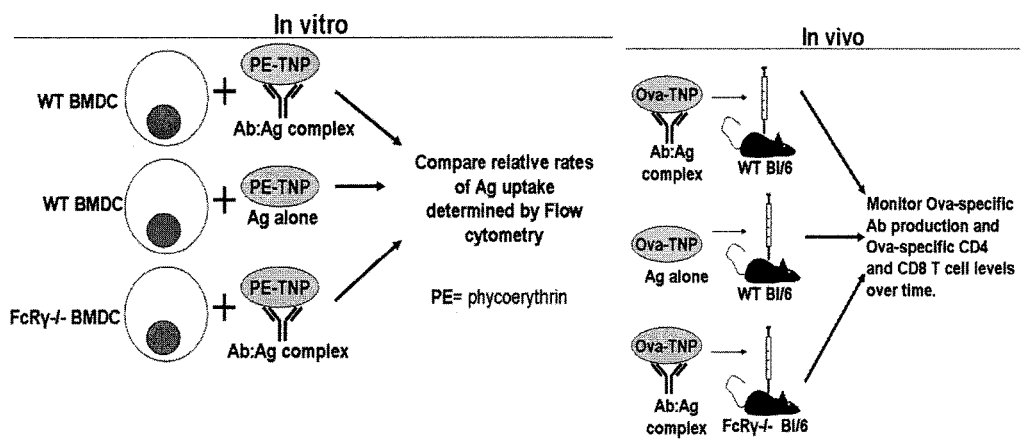
FIG. 4 shows the in vitro experimental design to test the role of secreted Ig and the in vivo experimental design for the role of soluble Ig in enhanced immune responses.

To test the role of secreted Ig in vitro, hapten-specific or pre-immune serum are incubated with the modified fluorochrome PE (phycoerythrin) or controls (TNP-PE, PE, or DP-PE; a non-specific hapten) (FIG. 4). BMDC (bone marrow derived DC) from WT and FcγR−/− mice (Takai, T., et al. 1994. Cell 76:519-529) are treated with the PE molecules. Fluorescent Ag associated with BMDCs is quantitated using flow cytometry. Ova cross-presentation is determined by staining BMDCs for MHC:ova-peptide expression using MHC:SIINFEKL (SEQ ID NO:3) specific Abs. The role of soluble Ig in enhanced immune responses in vivo is determined by injecting serum-absorbed ova i.p. into mice and monitoring lymphocyte responses. Serum and TB-LN are isolated and tested for ova-specific Abs, cytokines, and lineage specific markers as described above. The role of soluble Ig is determined via immunization in FcγR−/− mice, where FcγRI and III are nonfunctional (Takai, T., et al. 1994. Cell 76:519-529), which severely impairs APC phagocytosis of hapten-conjugated or Ab-opsonized Ag (Wernersson, S., et al. 1999. J Immunol 163:618-622). Conversely, the membrane IgM transgenic (tg) mouse CB-17, maintains a tg IgM H chain that cannot be secreted (Hannum, L. et al. 2000. J Exp Med 192:931-942). As CB-17 is H-chain Ig-tg, Ab repertoire is diminished. However, expression of H-chain mIgM with a λ L chain confers recognition of the hapten NP, resulting in 2-4% NP specific B cells (Hannum, L. et al. 2000. J Exp Med 192:931-942; Levine, M. et al. 2000. Proc Natl Acad Sci USA 97:2743-2748). CB-17 is used to determine the role of Ag-specific B cells as APCs in humoral-enhanced immunization. In each case the mutant mice and controls are given initial KLH-NP immunizations followed by Ova-NP, and Ova-specific responses are analyzed. CB-17 mice are not tested for serum Ig as they do not secrete Ab. Both CB-17 and FcγR−/− mice are commercially available.

Determination of Immune Effects of Repeated Immunization with ARE-Modified New Ags.

Continual production of ARE Abs may be deleterious due to regulatory B cell differentiation/expansion, interaction with inhibitory FcγRIIb, or masking responses to new ARE conjugated Ags via immune-complex clearance. These experiments identify potential limitations to humoral-enhanced responses to new ARE conjugated Ags, either concurrent or in succession (FIG. 5). Mice are first immunized against KLH-TNP (as described above) and then Ova-TNP at times determined for maximal T cell responses. Next, BSA-TNP is the immunogen, followed by HEL-TNP. After each new Ag, T cell responses to all received immunogens is monitored and compared to naïve and control immunized mice at 3 d intervals. While Ag-specific T cell responses to ova is determined by intracellular staining (ICS) using defined MHC class I and II peptides, the immunodominant peptides for PCC and HEL for B6 mice are unknown, so enumeration of PCC and HEL-specific T cells use Ag presenting BMDCs. Multivalent vaccines confer protection against multiple pathogens in one dose. It is determined whether enhanced adaptive immunity to all ARE-modified Ags is observed if multiple ARE-conjugated Ags are given simultaneously. Upon immunization with KLH-TNP, mice receive a multivalent vaccine containing Ova-TNP, HEL-TNP, and PCC-TNP. Controls receive vaccines to non-conjugated Ova, HEL, and PCC. As an additional control for ARE-independent amplification of responses, a group of KLH-TNP immunized mice receive a multivalent vaccine containing Ova-TNP, PCC-TNP, and non-conjugated HEL. Comparing the HEL specific immune responses from this group with the other two groups shows if there is ARE-independent adaptive immune enhancement when multivalent ARE-conjugated vaccines are given.

The above experiments compare the adaptive immune responses between mice that recognize ARE-conjugated Ags and those that do not. FIG. 2 indicates that pre-existing Ab responses enhance CD8 T cell responses to new Ag-conjugated AREs.

Determination of the Efficacy of ARE Modified Peptide Vaccines

The ARE strategy requires either immunizing with hapten:carrier conjugates or using epitopes recognized from prior immunizations. The Ig-immunodominant epitopes of many childhood vaccines are known and have potential as AREs conjugated to new Ags. The following experiment tests the protective levels of ARE conjugated vaccines vs. non-ARE vaccines and the usefulness of relevant human AREs vs. haptens.

Immunogenicity of ARE modified Influenza related peptides. Using the model described above, mice are immunized with KLH, KLH-TNP, KLH-tetanus toxoid (TT), or TT alone. Each group are then divided and immunized with TNP or TT-conjugated influenza protein A. Relative immune responses are then measured by influenza-specific Ab titer (ELISA), and Ag-specific T cell responses).

Vaccine-induced protection against influenza infection. ARE-modified as compared to traditional vaccination for protection from lethal intranasal influenza infection is examined A 1.0×LD50 of H1N1/mouse is delivered intranasally. At 2-day intervals T cells from the TB-LN is monitored by ICS after interaction with immunodominant peptides from Influenza NP Ag (Methods). Lung viral titer is enumerated/g tissue (Legge, K. L., and T. J. Braciale. 2005. *Immunity* 23:649-659). An enhanced adaptive immune response, measured by NP-specific T cell activity and Abs, is expected in mice immunized with TNP or TT conjugated KLH.

Determination of Effectiveness of the ARE Strategy in Reducing Need for Repeated Immunizations.

Enhanced immunity induced by ARE modification may reduce the need for booster shots, and thus yield higher immunization compliance. This is of particular importance in the developing world, where individuals often travel long distances for vaccination. The following experiment compare the immune response generated by traditional boosted immunization with that generated by a single immunization using an ARE modified vaccine. The Hepatitis B surface Ag (HBsAg) is used as an immunogen. Immunization with the Hep B vaccine (containing HBsAg) requires 3 injections (d0, 30, and 180). Compliance with the injection regimen is ~68% (Trevisan, A., et al. 2006. *Am J Infect Control* 34:465-466), due in part to time between vaccinations.

Mice are immunized with KLH-TNP as described above. Following seroconversion, mice receive either haptenated or equal amounts of non-haptenated HBsAg vaccine. Mice are monitored for B and T cell responses to HBsAg every 5 d post immunization. CD4 T cell responses are monitored by ICS in response to whole-Ag pulsed BMDCs. CD8 T cell responses specifically are measured using MHC class I specific peptides.

While information about effects of ARE modified Hep B vaccine on T cell responses is important, Ab titers correlate with protection against Hep B infection, so the emphasis is on Ag-specific Ab production.

Measurable Hep B specific humoral and cellular responses are expected after a single ARE-conjugated vaccine in contrast to three immunizations necessary with traditional Hep B immunizations. Level of adaptive immunity after 1-2 ARE-conjugated Hep B vaccinations is compared with responses generated by each of the three vaccinations with the traditional strategy.

Role of Soluble Ag-Specific Immunoglobulin in Enhanced Responses.

Briefly, serum from KLH or KLH-TNP immunized mice was incubated with TNP conjugated ovalbumin (FIG. 7). The resulting mixtures containing ovalbumin-TNP plus mouse serum or ovalbumin-TNP:antibody complexes were injected into naïve mice (3 per group). Seven days post ovalbumin injection the percent of ova-specific splenic CD8 T cells was determined by intracellular cytokine staining. Note that the injection of immune complexes using TNP as an ARE enhances the cellular response to the vaccine.

Determination of the Efficacy of ARE Modified Peptide Vaccines.

Mice with ARE specific antibodies show less morbidity after vaccination and challenge with Influenza (FIG. 8). Mice were either mock vaccinated (alum w/PBS) or immunized against Hepatitis B using the human vaccine (HBsAg—in alum). Upon sero-conversion to HBsAg in the test group, both groups of mice received a Hepatitis ARE tagged influenza nucleoprotein vaccine (HepPep—covalently linked to the nucleoprotein—NP—of influenza). Both groups were then challenged with virulent influenza and morbidity determined by weightloss. The HepPep-ARE tagged vaccine group shows less morbidity than the control group.

ARE-Ag Conjugated Compounds

The present invention provides compounds that are conjugates of AREs and antigens, which are optionally operably linked by means of a linker moiety.

A. Antibody Recognition Element (ARE)

An ARE (antibody recognition element) is a B cell epitope of any immunogen. To be used commercially, it is important that the ARE be recognized by a large pool of potential recipients. Therefore, AREs derived from commonly used recognition elements derived from prior vaccinations or naturally occurring infections for each recipient group are best.

The AREs of the present invention are peptides. In one embodiment, the ARE is the VP-1 epitope of polio of about 11-28 amino acids in length comprising IPALTAVETGA (SEQ ID NO: 1). In another embodiment, the ARE is a variant of this HBsAg epitope containing an N-terminal addition of RAGG (SEQ ID NO:10) onto the amino acid sequence. In another embodiment, the ARE is a variant of the HBsAg epitope in that it contains other amino acids that are used as spacers or reactive groups.

B. Antigens

The antigens that are linked to the AREs include proteinaceous components of known human and animal infectious agents, such as bacteria, fungus, parasites, prions and viruses, or cancer antigens. Examples of antigens that can be linked to the AREs are antigens from various infectious diseases that affect humans including the following:

Bacterial Infectious Diseases

Anthrax

Bacterial meningitis

Botulism
Brucellosis
Campylobacteriosis
Cat scratch disease
Cholera
Diphtheria
Epidemic Typhus
Gonorrhea
Impetigo
Legionellosis
Leprosy (Hansen's disease)
Leptospirosis
Listeriosis
Lyme disease
Melioidosis
MRSA infection
Nocardiosis (*Nocardia asteroides* or *Nocardia brasiliensis*)
Pertussis (Whooping cough)
Plague
Pneumococcal pneumonia
Psittacosis
Q fever
Rocky Mountain Spotted Fever
Salmonellosis
Scarlet fever:
Shigellosis
Syphilis
Tetanus
Trachoma
Tuberculosis
Tularemia
Typhoid fever
Typhus.
Urinary tract infections: cystitis or pyelonephritis
Fungal Infectious Diseases
Aspergillosis: allergic bronchopulmonary aspergillosis or pulmonary aspergilloma or invasive aspergillosis.
Blastomycosis
Candidiasis
Coccidioidomycosis
Cryptococcosis
Histoplasmosis
Tinea pedis
Parasitic Infections Diseases
African trypanosomiasis
Amebiasis
Ascariasis
Babesiosis
Chagas disease
Clonorchiasis
Cryptosporidiosis
Cysticercosis
Diphyllobothriasis
Dracunculiasis
Echinococcosis
Enterobiasis
Fascioliasis
Fasciolopsiasis
Filariasis
Free-living amebic infection (caused by *Naegleria fowleri* and *Acanthamoeba*)
Giardiasis
Gnathostomiasis
Hymenolepiasis (*Hymenolepis nana* or *Hymenolepis diminuta*)
Isosporiasis
Malaria
Metagonimiasis
Myiasis
Onchocerciasis
Pediculosis
Scabies
Taeniasis
Toxocariasis
Toxoplasmosis
Trichinellosis
Trichuriasis
Trichomoniasis
Trypanosomiasis
Prion Infectious Diseases
Alpers syndrome
Creutzfeldt-Jakob disease
Fatal familial insomnia
Kuru
Transmissible spongiform encephalopathy
Viral Infections Diseases
AIDS
Chickenpox (Varicella)
Common cold (acute viral nasopharyngitis)
Cytomegalovirus infection
Colorado tick fever
Dengue fever
Ebola haemorrhagic fever
Hand, foot and mouth disease (Coxsackie A virus)
Hepatitis
Herpes simplex
Herpes zoster
HPV
Influenza (Flu)
Lassa fever
Measles
Marburg haemorrhagic fever
Infectious mononucleosis.
Mumps
Poliomyelitis
Progressive multifocal leukencephalopathy
Rabies
Rubella
SARS
Smallpox (Variola): caused by Variola major and Variola minor.
Viral encephalitis
Viral gastroenteritis
Viral meningitis
Viral pneumonia
West Nile disease
Yellow fever The antigens of the present invention may also be of veterinary origin. See, e.g., Veterinary Microbiology $2^{nd}$ Edition; Hirsh, D C; MacLachlan, N J; and Walker, R L.; Blackwell Publishing.

In certain embodiments the Nucleocapsid Protein (NP) from Influenza A H5N1 (A/Indonesia/5/2005(H5N1)) Genebank protein accession number #ABI36003 is used as the antigen.

C. Couplers/Linkers

ARE-antigen coupling is done either directly or using chemical linkers in accord with conventional practice.

In certain embodiments, the ARE and antigen molecules are covalently linked using a chemical cross-linking agent. Many different cross-linking agents can be used. In certain embodiments the cross-linking agent is about 400-1000 daltons or about 3-12 angstroms in length. The cross-linkers useful in the present invention must be at least bivalent so that they can covalently join two molecules, the ARE to the antigen molecule. In certain embodiments, the cross-linker can be tris-succinimidyl aminotriacetate (TSAT); bis(sulfo-succinimidyl) suberate (BS3); disuccinimidyl suberate (DSS); bis(2-[sulfosuccinimidyooxycarbonloxy]ethylsulfone) (BOSCOES); bis(2-[succinimidyooxycarbonloxy]ethylsulfone) (Sulfo-BOSCOES); ethylene glycol bis-(succinimidylsuccinate) (EGS); ethylene glycol bis-(sulfosuccinimidylsuccinate) (Sulfo-EBS); or Dimethyl 3,3'-dithiobis-propionimidate (DTBP). In certain embodiments, the cross-linker is bivalent such as BS3, Sulfo-Boscoes, EGS, Sulfo-EBS, or DTBP.

Methods for attaching cross-linkers are well known in the art (c.f. Hermanson, 1995 Bioconjugate Techniques, Academic Press, Inc. New York, pp. 728; Wong, 1991 Chemistry of Protein Conjugation and Cross-linking. CRC Press, pp. 340; Brinkley, 1992 A brief survey of methods for preparing protein conjugates with dyes, haptens and cross-linking reagents Bioconjugate Chem. 3:2-13).

Examples of suitable linkers include formaldehyde, gluteraldehyde, MBS (m-Maleimidobenzoyl-N-hydroxysuccinimide ester) and/or Sulfo-MBS (the water soluble analog of MBS), etc. Examples of couplers/linkers are described in detail on the world-wide-web at solulink.com/white_papers/peptide and at piercenet.com and at piercenet.com/products/browse.cfm?fldID=020306.

General Methods and Procedures:

Ag conjugation. KLH-TNP and ova-TNP are commercially available (Biosearch Technologies). Additional conjugates are made by reduction using TNP-e-Aminocaproyl-O-Su (Biosearch) in the presence of vaccine Ags. T cell activity is monitored by ICS. Peritoneal draining TB-LN is harvested as described above. LN is homogenized and cell number/LN enumerated. Cell suspensions are treated with or without Ag-specific MHC class I or class II restricted peptides (Table 2) in the presence of brefeldin A and incubated for 6 h.

BMDCs are pulsed with Ag for 24 h allowing the cells to process and present via MHC class II. Because CD8+ T cell Ags are more efficiently generated from intracellular sources, the loading of MHC class I is accomplished by transfecting BMDCs with DNA encoding the desired Ag. After transfection the BMDCs are allowed 36 h to produce, process, and present Ag. These BMDCs, together with nonpulsed-BMDCs, are then used as APCs for stimulation of T cells derived from the TB-LN.

Humoral response analysis is performed by measuring Ag-specific serum Abs. Ag-specific ELISAs are as previously described (Xie, P., et al. 2007. *Immunity* 27:253-267; Stunz, L. et al. 2004. *Immunity* 21:255-266). 20 Abs to mouse IgM and IgG are used to detect Ag-specific serum Abs. OD readings>2 fold above background are considered positive (Xie, P., et al. 2007. *Immunity* 27:253-267; Stunz, L. et al. 2004. *Immunity* 21:255-266). Cytokines are measured in serum and cell cultures using multiplex Luminex. Serum samples are collected during LN harvest. Cells isolated from the TB-LN are stimulated with peptides as described. Supernatants are collected after 24 h and subjected to multiplex cytokine assays.

Immune Banking

Current adjuvant systems induce global, non-specific immune activity that can result in inflammation, tissue damage, or even autoimmune disease-like syndromes. One of the novel advantages of the Immune Banking process is the use of pre-existing antibodies as endogenous adjuvants, able to induce a robust immune response. In contrast to current adjuvants, however, this response is highly specific to the immunizing antigen, and does not result in global, non-specific immune triggering. Because the pre-existing immune response Immune Baking exploits is created and sustained by the recipient as a natural defense against foreign biomolecules, this technology reduces adjuvant side-effects and is better tolerated by recipients.

TABLE 2

| Mouse strain | Antigen | MHC class I epitope | MHC class II epitope |
|---|---|---|---|
| CH57BI/6 | ovalbumin | SIINFEKL (SEQ ID NO. 3) | ISQAVHAAHAEINEAGR (SEQ ID NO. 6) |
| CH57BI/6 | Influ-NP | ASNENMETM (SEQ ID NO. 34) | QVYSLIRPNENPAHK (SEQ ID NO. 7) |
| CH57BI/6 | Influ-NP | Unknown | RSALILRGSVAHKSC (SEQ ID NO. 8) |
| CH57BI/6 | PCC | Unknown | Unknown |
| CH57BI/6 | HEL | Unknown | Unknown |
| CH57BI/6 | HBsAg | IPQSLDSWWTSL (SEQ ID NO. 5) | CTTPAQGNSMFPSCCCTKPTD GNC (SEQ ID NO. 9) |

Figure 6:
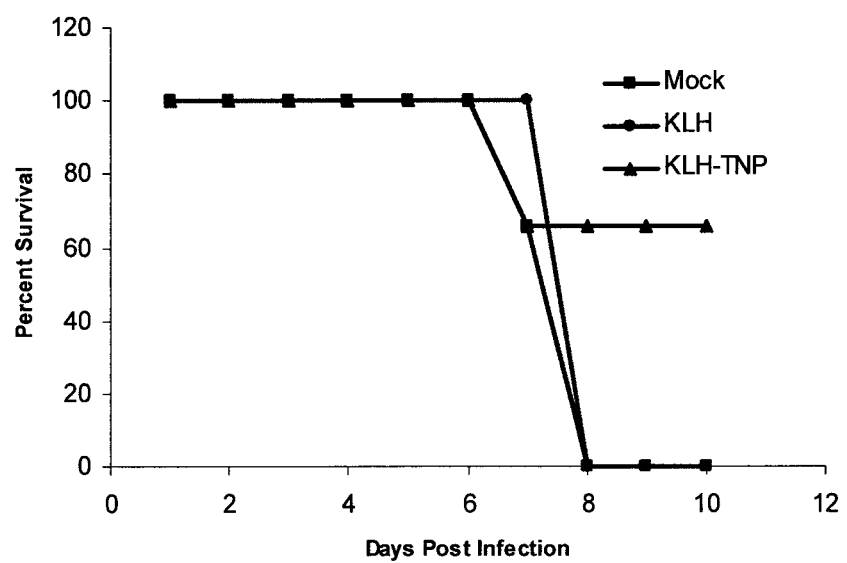
FIG. 6 shows Immune Banking, which is the exploitation of pre-existing Ab response to an ARE hapten, 2,4,6, Trinitrophenyl (TNP), provides protection against influenza induced death.
Figure 9:
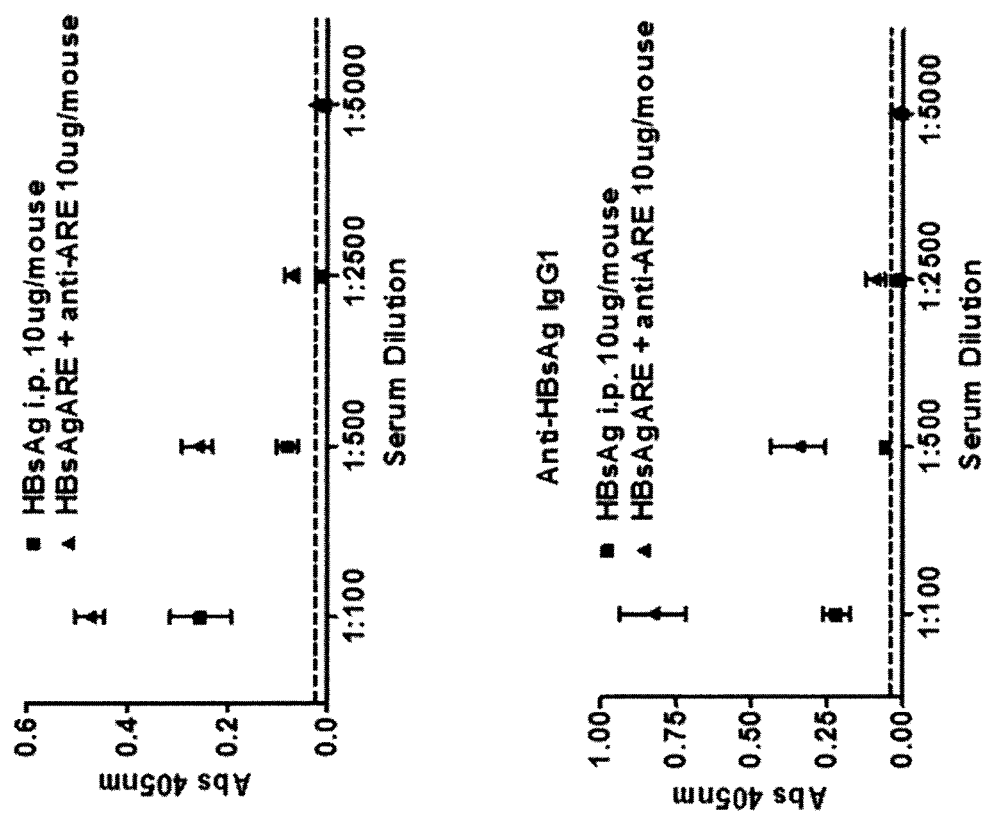
FIG. 9 shows the results of VP-1 ARE chemically linked to the HBsAg and given as an immune complex.

Samples are stained for surface expression markers of T cell subsets, fixed and permeabilized, and stained for intracellular IFN-γ. Flow cytometry determines the % of IFN-γ+ (Ag-responsive) CD4+ and CD8+ T cells (Kraus, Z. J., et al. 2008. *J Immunol* 181:7800-7809). If MHC class I and class II immunodominant peptides are unknown (Table 2), syngeneic BMDCs are generated and used as APCs (Breckpot, K., et al. 2004. *J Gene Med* 6:1175-1188; Sudowe, S., et al. 2003. *Mol Ther* 8:567-575; Bros, M., et al. 2009. *J Immunol Methods* 343:13-20). To stimulate Ag specific CD4 T cells, In one example, Immune Banking exploited pre-existing Ab response to an ARE hapten, TNP, and provided protection against influenza induced death. Mice vaccinated with alum alone, KLH in alum, or KLH-TNP in alum were immunized against influenza using a TNP-haptenated recombinant nucleocapsid protein (NP) of influenza (FIG. 6). Mice were then infected with a lethal dose of influenza and monitored for disease. Mice immunized with KLH-TNP showed a 66% survival rate compared to the control groups with 0% survival.

Linking of ARE to Antigens

In certain embodiments, VP-1 ARE were chemically linked to the HBsAg and administered as an immune complex. In other words, the HBsAg was chemically linked to the VP-1 ARE and then mixed with an antibody that recognizes the ARE. The complex of ARE-tagged HBsAg+Antibody was then injected as a vaccine and compared to HBsAg without antibody. The result was a robust immune response to the HBsAg as measured by generation of HBsAg-specific antibodies.

In certain embodiments, the ARE was linked to the antigen through recombinant DNA technology, i.e., the construct was made as a fusion protein that effectively functions as an ARE.

Vaccines of the Invention

In certain embodiments, the present invention provides vaccines for use to protect mammals against the colonization and/or infection of infectious agents or to treat cancer.

"Hapten" refers to a low-molecular weight organic compound that is not capable of eliciting an immune response by itself but will elicit an immune response once attached to a carrier molecule. Exemplary haptens used in conjugated compounds, compositions and methods of the invention include drugs, hormones and toxins, but are not limited to these specific haptens.

The term "epitope" refers to basic element or smallest unit of recognition by an individual antibody or T-cell receptor, and thus the particular domain, region or molecular structure to which said antibody or T-cell receptor binds. An antigen may consist of numerous epitopes while a hapten, typically, may possess few epitopes. As used herein "correspond essentially to" refers to an epitope that will elicit an immunological response at least substantially equivalent to the response generated by the native epitope. An immunological response to a composition or vaccine is the development in the host of a cellular and/or antibody-mediated immune response to the polypeptide or vaccine of interest. Usually, such a response consists of the subject producing antibodies, B cell, helper T cells, suppressor T cells, and/or cytotoxic T cells directed specifically to an antigen or antigens included in the composition or vaccine of interest. Vaccines of the present invention can also include effective amounts of immunological adjuvants, known to enhance an immune response. An "effective amount" refers to an amount necessary or sufficient to realize a desired biologic effect. An effective amount of the composition would be the amount that achieves this selected result, and such an amount could be determined as a matter of routine by a person skilled in the art. For example, an effective amount for treating an immune system deficiency could be that amount necessary to cause activation of the immune system, resulting in the development of an antigen specific immune response upon exposure to antigen. The term is also synonymous with "sufficient amount." The effective amount for any particular application can vary depending on such factors as the disease or condition being treated, the particular composition being administered, the size of the subject, and/or the severity of the disease or condition. One of ordinary skill in the art can empirically determine the effective amount of a particular composition of the present invention without necessitating undue experimentation.

The term "adjuvant" as used herein refers to non-specific stimulators of the immune response or substances that allow generation of a depot in the host, which when combined with the vaccine and pharmaceutical composition, respectively, of the present invention may provide for an even more enhanced immune response. A variety of adjuvants can be used. Examples include complete and incomplete Freund's adjuvant, aluminum hydroxide and modified muramyldipeptide. Further adjuvants are mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art. Further adjuvants that can be administered with the compositions of the invention include, but are not limited to, Monophosphoryl lipid immunomodulator, AdjuVax 100a, QS-21, QS-18, CRL1005, Aluminum salts (Alum), MF-59, OM-174, OM-197, OM-294, and Virosomal adjuvant technology. The adjuvants can also comprise a mixture of these substances.

To immunize a subject, the composition is administered parenterally, usually by intramuscular or subcutaneous injection in an appropriate vehicle. Other modes of administration, however, such as oral, intranasal or intradermal delivery, are also acceptable.

Vaccine formulations will contain an effective amount of the active ingredient in a vehicle, the effective amount being readily determined by one skilled in the art. The active ingredient may typically range from about 1% to about 95% (w/w) of the composition, or even higher or lower if appropriate. The quantity to be administered depends upon factors such as the age, weight and physical condition of the animal or the human subject considered for vaccination. The quantity also depends upon the capacity of the animal's immune system to synthesize antibodies, and the degree of protection desired. Effective dosages can be readily established by one of ordinary skill in the art through routine trials establishing dose response curves. The subject is immunized by administration of the biofilm peptide or fragment thereof in one or more doses. Multiple doses may be administered as is required to maintain a state of immunity to the bacterium of interest.

Intranasal formulations may include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

To prepare a vaccine, the purified composition can be isolated, lyophilized and stabilized. The composition may then be adjusted to an appropriate concentration, optionally combined with a suitable vaccine adjuvant, and packaged for use. Suitable adjuvants include but are not limited to surfactants, e.g., hexadecylamine, octadecylamine, lysolecithin, dimethyldioctadecylammonium bromide, N,N-dioctadecyl-N'—N-bis(2-hydroxyethyl-propane di-amine), methoxyhexadecyl-glycerol, and pluronic polyols; polanions, e.g., pyran, dextran sulfate, poly IC, polyacrylic acid, carbopol; peptides, e.g., muramyl dipeptide, aimethylglycine, tuftsin, oil emulsions, alum, and mixtures thereof. Other potential adjuvants include the B peptide subunits of *E. coli* heat labile toxin or of the cholera toxin. McGhee, J. R., et al., "On vaccine development," *Sem. Hematol.,* 30:3-

15 (1993). Finally, the immunogenic product may be incorporated into liposomes for use in a vaccine formulation, or may be conjugated to proteins such as keyhole limpet hemocyanin (KLH) or human serum albumin (HSA) or other polymers.

Definitions

"Bound" refers to binding or attachment that may be covalent, e.g., by chemically coupling, or non-covalent, e.g., ionic interactions, hydrophobic interactions, hydrogen bonds. Covalent bonds can be, for example, ester, ether, phosphoester, amide, peptide, imide, carbon-sulfur bonds, carbon-phosphorus bonds, and the like. The term "bound" is broader than and includes terms such as "conjugated," "coupled," "fused" and "attached."

The terms "protein," "peptide" and "polypeptide" are used interchangeably herein. The invention encompasses isolated or substantially purified protein compositions. In the context of the present invention, an "isolated" or "purified" polypeptide is a polypeptide that exists apart from its native environment and is therefore not a product of nature. A polypeptide may exist in a purified form or may exist in a non-native environment such as, for example, a transgenic host cell. For example, an "isolated" or "purified" protein, or biologically active portion thereof, is substantially free of other cellular material, or culture medium when produced by recombinant techniques, or substantially free of chemical precursors or other chemicals when chemically synthesized. A protein that is substantially free of cellular material includes preparations of protein or polypeptide having less than about 30%, 20%, 10%, 5%, (by dry weight) of contaminating protein. When the protein of the invention, or biologically active portion thereof, is recombinantly produced, preferably culture medium represents less than about 30%, 20%, 10%, or 5% (by dry weight) of chemical precursors or non-protein-of-interest chemicals. Fragments and variants of the disclosed proteins or partial-length proteins encoded thereby are also encompassed by the present invention. By "fragment" or "portion" is meant a full length or less than full length of the amino acid sequence of, a polypeptide or protein.

"Naturally occurring" is used to describe an object that can be found in nature as distinct from being artificially produced. For example, a protein or nucleotide sequence present in an organism (including a virus), which can be isolated from a source in nature and which has not been intentionally modified by man in the laboratory, is naturally occurring.

A "variant" of a molecule is a sequence that is substantially similar to the sequence of the native molecule.

"Wild-type" refers to the normal gene, or organism found in nature without any known mutation.

"Operably-linked" refers to the association of molecules so that the function of one is affected by the other.

The term "substantial identity" in the context of a peptide indicates that a peptide comprises a sequence with at least 70%, 71%, 72%, 73%, 74%, 75%, 76%, 77%, 78%, or 79%, 80%, 81%, 82%, 83%, 84%, 85%, 86%, 87%, 88%, or 89%, at least 90%, 91%, 92%, 93%, or 94%, or 95%, 96%, 97%, 98% or 99%, sequence identity to a reference sequence over a specified comparison window. Optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may results form, for example, genetic polymorphism or from human manipulation. Methods for such manipulations are generally known in the art.

Thus, the polypeptides of the invention may be altered in various ways including amino acid substitutions, deletions, truncations, and insertions. Methods for such manipulations are generally known in the art. For example, amino acid sequence variants of the polypeptides can be prepared by mutations in the DNA. Methods for mutagenesis and nucleotide sequence alterations are well known in the art. See, for example, Kunkel, Proc. Natl. Acad. Sci. USA, 82:488 (1985); Kunkel et al., Meth. Enzymol., 154:367 (1987); U.S. Pat. No. 4,873,192; Walker and Gaastra, Techniques in Mol. Biol. (MacMillan Publishing Co. (1983), and the references cited therein. Guidance as to appropriate amino acid substitutions that do not affect biological activity of the protein of interest may be found in the model of Dayhoff et al., Atlas of Protein Sequence and Structure (Natl. Biomed. Res. Found. 1978). Conservative substitutions, such as exchanging one amino acid with another having similar properties, are preferred.

Thus, the polypeptides of the invention encompass naturally occurring proteins as well as variations and modified forms thereof. Such variants will continue to possess the desired activity. The deletions, insertions, and substitutions of the polypeptide sequence encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by routine screening assays.

Individual substitutions deletions or additions that alter, add or delete a single amino acid or a small percentage of amino acids (typically less than 5%, more typically less than 1%) in an encoded sequence are "conservatively modified variations," where the alterations result in the substitution of an amino acid with a chemically similar amino acid. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q). In addition, individual substitutions, deletions or additions which alter, add or delete a single amino acid or a small percentage of amino acids in an encoded sequence are also "conservatively modified variations."

As used herein, the term "therapeutic agent" refers to any agent or material that has a beneficial effect on the mammalian recipient. Thus, "therapeutic agent" embraces both therapeutic and prophylactic molecules having nucleic acid or protein components.

"Treating" as used herein refers to ameliorating at least one symptom of, curing and/or preventing the development of a given disease or condition.

"Antigen" refers to a molecule capable of being bound by an antibody. An antigen is additionally capable of being recognized by the immune system and/or being capable of inducing a humoral immune response and/or cellular immune response leading to the activation of B- and/or T-lymphocytes. An antigen can have one or more epitopes (B- and/or T-cell epitopes). Antigens as used herein may also be mixtures of several individual antigens. "Antigenic determinant" refers to that portion of an antigen that is specifically recognized by either B- or T-lymphocytes. B-lymphocytes responding to antigenic determinants produce antibodies, whereas T-lymphocytes respond to antigenic determinants by proliferation and establishment of effector functions critical for the mediation of cellular and/or humoral immunity.

As used herein, the term "antibody" refers to molecules capable of binding an epitope or antigenic determinant. This term includes whole antibodies and antigen-binding fragments thereof, including single-chain antibodies. In certain embodiments, the antibodies are human antigen binding antibody fragments and include, but are not limited to, Fab, Fab' and F(ab')$_2$, Fd, single-chain Fvs (scFv), single-chain antibodies, disulfide-linked Fvs (sdFv) and fragments comprising either a $V_L$ or $V_H$ domain. The antibodies can be from any animal origin including birds (e.g. chicken) and mammals (e.g., human, murine, rabbit, goat, guinea pig, camel, horse and the like). As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described, for example, in U.S. Pat. No. 5,939,598.

As used herein, the term "monoclonal antibody" refers to an antibody obtained from a group of substantially homogeneous antibodies, that is, an antibody group wherein the antibodies constituting the group are homogeneous except for naturally occurring mutants that exist in a small amount. Monoclonal antibodies are highly specific and interact with a single antigenic site. Furthermore, each monoclonal antibody targets a single antigenic determinant (epitope) on an antigen, as compared to common polyclonal antibody preparations that typically contain various antibodies against diverse antigenic determinants. In addition to their specificity, monoclonal antibodies are advantageous in that they are produced from hybridoma cultures not contaminated with other immunoglobulins.

The adjective "monoclonal" indicates a characteristic of antibodies obtained from a substantially homogeneous group of antibodies, and does not specify antibodies produced by a particular method. For example, a monoclonal antibody to be used in the present invention can be produced by, for example, hybridoma methods (Kohler and Milstein, Nature 256:495, 1975) or recombination methods (U.S. Pat. No. 4,816,567). The monoclonal antibodies used in the present invention can be also isolated from a phage antibody library (Clackson et al., Nature 352:624-628, 1991; Marks et al., J. Mol. Biol. 222:581-597, 1991). The monoclonal antibodies of the present invention particularly comprise "chimeric" antibodies (immunoglobulins), wherein a part of a heavy (H) chain and/or light (L) chain is derived from a specific species or a specific antibody class or subclass, and the remaining portion of the chain is derived from another species, or another antibody class or subclass. Furthermore, mutant antibodies and antibody fragments thereof are also comprised in the present invention (U.S. Pat. No. 4,816,567; Morrison et al., Proc. Natl. Acad. Sci. USA 81:6851-6855, 1984).

As used herein, the term "mutant antibody" refers to an antibody comprising a variant amino acid sequence in which one or more amino acid residues have been altered. For example, the variable region of an antibody can be modified to improve its biological properties, such as antigen binding. Such modifications can be achieved by site-directed mutagenesis (see Kunkel, Proc. Natl. Acad. Sci. USA 82: 488 (1985)), PCR-based mutagenesis, cassette mutagenesis, and the like. Such mutants comprise an amino acid sequence which is at least 70% identical to the amino acid sequence of a heavy or light chain variable region of the antibody, more preferably at least 75%, even more preferably at least 80%, still more preferably at least 85%, yet more preferably at least 90%, and most preferably at least 95% identical. As used herein, the term "sequence identity" is defined as the percentage of residues identical to those in the antibody's original amino acid sequence, determined after the sequences are aligned and gaps are appropriately introduced to maximize the sequence identity as necessary.

Specifically, the identity of one nucleotide sequence or amino acid sequence to another can be determined using the algorithm BLAST, by Karlin and Altschul (Proc. Natl. Acad. Sci. USA, 90: 5873-5877, 1993). Programs such as BLASTN and BLASTX were developed based on this algorithm (Altschul et al., J. Mol. Biol. 215: 403-410, 1990). To analyze nucleotide sequences according to BLASTN based on BLAST, the parameters are set, for example, as score=100 and wordlength=12. On the other hand, parameters used for the analysis of amino acid sequences by BLASTX based on BLAST include, for example, score=50 and wordlength=3. Default parameters for each program are used when using the BLAST and Gapped BLAST programs. Specific techniques for such analyses are known in the art (see the website of the National Center for Biotechnology Information (NCBI), Basic Local Alignment Search Tool (BLAST); http://www.ncbi.nlm.nih.gov). Polyclonal and monoclonal antibodies can be prepared by methods known to those skilled in the art. For example, the antibodies can be prepared by the methods described below.

An antigen prepared as described above is given to a mammal, such as a mouse, rat, hamster, guinea pig, horse, monkey, rabbit, goat, and sheep. This immunization can be performed by any existing method, including typically used intravenous injections, subcutaneous injections, and intraperitoneal injections. There are no restrictions as to the immunization intervals. Immunization may be carried out at intervals of several days to several weeks, preferably four to 21 days. A mouse can be immunized, for example, at a single dose of 10 to 100 µg (for example, 20 to 40 µg) of the antigen protein, but the dose is not limited to these values.

Before the first immunization, and three to seven days after the second and subsequent immunizations, blood is collected from the animals, and the sera are analyzed for antibody titer. To promote an immune response, an aggregating agent such as alum is preferably used. In general, selected mammalian antibodies have sufficiently high antigen binding affinity. Antibody affinity can be determined using a saturation binding assay, an enzyme-linked immunosorbent assay (ELISA), or a competitive assay (for example, radioimmunoassay).

Polyclonal antibodies can be screened by a conventional crosslinking analysis, such as that described in "Antibodies, A Laboratory Manual (Cold Spring Harbor Laboratories, Harlow and David Lane edit. (1988))." An alternative method is, for example, epitope mapping (Champe et al., J. Biol. Chem. 270:1388-1394 (1995)). A preferred method for determining polypeptide or antibody titers comprises quantifying antibody-binding affinity. In other embodiments, methods for assessing one or more biological properties of an antibody are also used in addition to or instead of the methods for determining antibody-binding affinity Such analytical methods are particularly useful because they demonstrate the therapeutic effectiveness of antibodies. When an antibody exhibits an improved property in such analysis, its binding affinity is generally, but not always, enhanced.

Hybridomas that are used to prepare monoclonal antibodies can be obtained, for example, by the method of Milstein et al. (Kohler, G., and Milstein, C., Methods Enzymol. 1981, 73, 3-46). Myeloma cells to be fused with antibody-producing cells may be cell lines derived from any of the various animals, such as mice, rats, and humans, which are generally available to those skilled in the art. The cell lines to be used are drug-resistant, and cannot survive in a selective medium (e.g., HAT medium) in an unfused state, but can survive in a fused state. 8-azaguanine-resistant cell lines are generally used, which are deficient in hypoxanthine-guanine-phosphoribosyl transferase and cannot grow in a hypoxanthine-aminopterin-thymidine (HAT) medium. Myeloma cells include a variety of known cell lines, for example, P3x63Ag8.653 (J. Immunol. (1979) 123: 1548-1550), P3x63Ag8U.1 (Current Topics in Microbiology and Immunology (1978) 81: 1-7), NS-1 (Kohler, G. and Milstein, C., Eur. J. Immunol. (1976) 6: 511-519), MPC-11 (Margulies, D. H. et al., Cell (1976) 6: 405-415), SP2/0 (Shulman, M. et al., Nature (1978) 276: 269-270), F0 (de St. Groth, S. F. et al., J. Immunol. Methods (1980) 35: 1-21), 5194 (Trowbridge, I. S., J. Exp. Med. (1978) 148: 313-323), 8210 (Galfre, G. et al., Nature (1979) 277: 131-133), and P3U1 (J. Exp. Med. 1979, 150:580; Curr Top Microbiol. Immunol. 1978, 81:1). Human myeloma and mouse-human heteromycloma cell lines can also be used to produce human monoclonal antibodies (Kozbar, J. Immunol. 133:3001 (1984); Brodeur et al., Monoclonal Antibody Production Techniques and Application, pp. 51-63 (Marcel Dekker, Inc., New York, 1987)). Antibody-producing cells are collected, for example, from animals sacrificed two to three days after the final immunization. Antibody-producing cells include spleen cells, lymph node cells, and peripheral blood cells. Spleen cells are generally used. Specifically, tissues such as spleens or lymph nodes are excised or collected from the various animals described above. Then, the tissues are crushed and the resulting material is suspended in a medium or buffer, such as PBS, DMEM, or RPMI1640, followed by filtration with a stainless mesh or the like. This is then centrifuged to obtain antibody-producing cells of interest.

The above-described myeloma cells and antibody-producing cells are then fused. Cell fusion is achieved by contacting the myeloma cells with the antibody-producing cells at a ratio of 1:1 to 1:20 in a medium for animal cell culture, such as MEM, DMEM, and RPMI-1640, at 30 to 37° C. for one to 15 minutes in the presence of a fusion-promoting agent. To promote cell fusion, the antibody-producing cells and the myeloma cells may be fused using a commercially available cell-fusion device, using a fusion-promoting agent, such as polyethylene glycol (mean molecular weight 1,000 to 6,000 (Da)) or polyvinyl alcohol, or a virus for fusion, such as Sendai virus.

Hybridomas of interest are selected from the cells after cell fusion. The selection methods include methods using selective propagation of cells in a selective medium. Specifically, a cell suspension is diluted with an appropriate medium, and then the cells are plated on to microtiter plates. An aliquot of selection medium (for example, HAT medium) is added to each well, and then the cells are cultured while the selection medium is appropriately exchanged. The cells grown as a result can be saved as hybridomas.

In another embodiment, antibodies or antibody fragments can be isolated from an antibody phage library, produced by using the technique reported by McCafferty et al. (Nature 348:552-554 (1990)). Clackson et al. (Nature 352:624-628 (1991)) and Marks et al. (J. Mol. Biol. 222:581-597 (1991)) reported on the respective isolation of mouse and human antibodies from phage libraries. There are also reports that describe the production of high affinity (nM range) human antibodies based on chain shuffling (Marks et al., Bio/Technology 10:779-783 (1992)), and combinatorial infection and in vivo recombination, which are methods for constructing large-scale phage libraries (Waterhouse et al., Nucleic Acids Res. 21:2265-2266 (1993)). These technologies can also be used to isolate monoclonal antibodies, instead of using conventional hybridoma technology for monoclonal antibody production.

Methods for preparing monoclonal antibodies from the obtained hybridomas include standard cell culture methods and methods comprising ascites production. In cell culture methods, hybridomas are cultured for two to 14 days under standard culture conditions (for example, at 37° C. at 5% $CO_2$ atmosphere), in a culture medium for animal cells, such as RPMI-1640 or MEM containing 10 to 20% fetal calf serum, or serum-free medium, and antibodies are then prepared from the culture supernatant. In the method comprising ascites production, hybridomas are administered to the peritoneal cavities of mammalian individuals of the same species as that from which the myeloma cells are derived, and the hybridomas proliferate in to large quantities. Ascites or serum is then collected after one to four weeks. To enhance ascites production, for example, pristane (2,6,10, 14-tetramethylpentadecane) may be pre-administered to the peritoneal cavity. Antibodies to be used in the present invention can be purified by a method appropriately selected from known methods, such as the protein A-Sepharose method, hydroxyapatite chromatography, salting-out method with sulfate, ion exchange chromatography, and affinity chromatography, or by the combined use of the same.

The present invention may use recombinant antibodies, produced by gene engineering. The genes encoding the antibodies obtained by a method described above are isolated from the hybridomas. The genes are inserted into an appropriate vector, and then introduced into a host (see, e.g., Carl, A. K. Borrebaeck, James, W. Larrick, Therapeutic Monoclonal Antibodies, Published in the United Kingdom by Macmillan Publishers Ltd, 1990). The present invention provides the nucleic acids encoding the antibodies of the present invention, and vectors comprising these nucleic acids. Specifically, using a reverse transcriptase, cDNAs encoding the variable regions (V regions) of the antibodies are synthesized from the mRNAs of hybridomas. After obtaining the DNAs encoding the variable regions of antibodies of interest, they are ligated with DNAs encoding desired constant regions (C regions) of the antibodies, and the resulting DNA constructs are inserted into expression vectors. Alternatively, the DNAs encoding the variable regions of the antibodies may be inserted into expression vectors comprising the DNAs of the antibody C regions. These are inserted into expression vectors so that the genes are expressed under the regulation of an expression regulatory region, for example, an enhancer and promoter. Then, host cells are transformed with the expression vectors to express the antibodies. The present invention provides cells expressing antibodies of the present invention. The cells expressing antibodies of the present invention include cells and hybridomas transformed with a gene of such an antibody.

In the present invention, recombinant antibodies artificially modified to reduce heterologous antigenicity against humans can be used. Examples include chimeric antibodies and humanized antibodies. These modified antibodies can be produced using known methods. A chimeric antibody includes an antibody comprising variable and constant regions of species that are different to each other, for example, an antibody comprising the antibody heavy chain and light chain variable regions of a nonhuman mammal such as a mouse, and the antibody heavy chain and light chain constant regions of a human. Such an antibody can be obtained by (1) ligating a DNA encoding a variable region of a mouse antibody to a DNA encoding a constant region of a human antibody; (2) incorporating this into an expression vector; and (3) introducing the vector into a host for production of the antibody.

A humanized antibody, which is also called a reshaped human antibody, is obtained by substituting an H or L chain complementarity determining region (CDR) of an antibody of a nonhuman mammal such as a mouse, with the CDR of a human antibody. Conventional genetic recombination techniques for the preparation of such antibodies are known (see, for example, Jones et al., *Nature* 321: 522-525 (1986); Reichmann et al., *Nature* 332: 323-329 (1988); Presta *Curr. Op. Struct. Biol.* 2: 593-596 (1992)). Specifically, a DNA sequence designed to ligate a CDR of a mouse antibody with the framework regions (FRs) of a human antibody is synthesized by PCR, using several oligonucleotides constructed to comprise overlapping portions at their ends. A humanized antibody can be obtained by (1) ligating the resulting DNA to a DNA that encodes a human antibody constant region; (2) incorporating this into an expression vector; and (3) transfecting the vector into a host to produce the antibody (see, European Patent Application No. EP 239,400, and International Patent Application No. WO 96/02576). Human antibody FRs that are ligated via the CDR are selected where the CDR forms a favorable antigen-binding site. The humanized antibody may comprise additional amino acid residue(s) that are not included in the CDRs introduced into the recipient antibody, nor in the framework sequences. Such amino acid residues are usually introduced to more accurately optimize the antibody's ability to recognize and bind to an antigen. For example, as necessary, amino acids in the framework region of an antibody variable region may be substituted such that the CDR of a reshaped human antibody forms an appropriate antigen-binding site (Sato, K. et al., *Cancer Res.* (1993) 53, 851-856).

Methods for obtaining human antibodies are also known. For example, desired human antibodies with antigen-binding activity can be obtained by (1) sensitizing human lymphocytes with antigens of interest or cells expressing antigens of interest in vitro; and (2) fusing the sensitized lymphocytes with human myeloma cells such as U266 (see Examined Published Japanese Patent Application No. (JP-B) Hei 1-59878). Alternatively, the desired human antibody can also be obtained by using an antigen to immunize a transgenic (Tg) animal that comprises a partial or entire repertoire of human antibody genes (see Nature Genetics 7:13-21 (1994); Nature Genetics 15:146-156 (1997); Nature 368: 856-859 (1994); International Patent Application WO 93/12227, WO 92/03918, WO 94/02602, WO 94/25585, WO 96/34096, and WO 96/33735). Specifically, such Tg animals are created as follows: a nonhuman mammal in which the loci of heavy and light chains of an endogenous immunoglobulin have been disrupted, and instead, the loci of heavy and light chains of a human immunoglobulin have been introduced via Yeast artificial chromosome (YAC) vectors and the like, is obtained by creating knockout animals or Tg animals, or mating such animals. The immunoglobulin heavy chain loci can be functionally inactivated, for example, by introducing a defect at a certain site in a J region or C region (e.g., Cμ region). The immunoglobulin light chains (e.g., κ chain) can be functionally inactivated, for example, by introducing a defect at a certain site in a J region or C region, or a region comprising the J and C regions.

Such a humanized antibody can also be obtained from culture supernatant, by using genetic engineering technology to transform eukaryotic cells with cDNAs that encode each of the heavy and light chains of the antibody, or preferably vectors comprising these cDNAs, and then culturing the transformed cells that produce the recombinant human monoclonal antibody. The hosts are, for example, desired eukaryotic cells, preferably mammalian cells, such as CHO cells, lymphocytes, and myelomas.

Furthermore, techniques to obtain human antibodies by panning with a human antibody library are known. For example, the variable region of a human antibody is expressed as a single chain antibody (scFv) on the surface of a phage, using phage display method, and phages that bind to the antigen can be selected. By analyzing the genes of selected phages, the DNA sequences encoding the variable regions of human antibodies that bind to the antigen can be determined. If the DNA sequences of scFvs that bind to the antigen are identified, appropriate expression vectors comprising these sequences can be constructed, and then introduced into appropriate hosts and expressed to obtain human antibodies. Such methods are already well known (see WO 92/01047, WO 92/20791, WO 93/06213, WO 93/11236, WO 93/19172, WO 95/01438, and WO 95/15388).

When the antibody genes have been isolated and introduced into an appropriate host, hosts and expression vectors can be used in appropriate combination to produce the antibodies. As eukaryotic host cells, animal cells, plant cells, and fungal cells may be used. The animal cells include: (1) mammalian cells such as CHO, COS, myeloma, baby hamster kidney (BHK), HeLa, and Vero cells; (2) amphibian cells such as *Xenopus* oocytes; or (3) insect cells such as sf9, sf21, and Tn5, or silkworms. Known plant cells include cells derived from the *Nicotiana* genus such as *Nicotiana tabacum*, which can be callus cultured. Known fungal cells include yeasts such as the *Saccharomyces* genus, for example *Saccharomyces cerevisiae*, and filamentous fungi such as the *Aspergillus* genus, for example *Aspergillus niger*. Prokaryotic cells can also be used in production systems that utilize bacterial cells. Known bacterial cells include *E. coli* and *Bacillus subtilis*. The antibodies can be obtained by transferring the antibody genes of interest into these cells using transformation, and then culturing the transformed cells in vitro.

The isotypes of the antibodies of the present invention are not limited. The isotypes include, for example, IgG (IgG1, IgG2, IgG3, and IgG4), IgM, IgA (IgA1 and IgA2), IgD, and IgE. The antibodies of the present invention may also be antibody fragments comprising a portion responsible for antigen binding, or a modified fragment thereof. The term "antibody fragment" refers to a portion of a full-length antibody, and generally to a fragment comprising an antigen-binding domain or a variable region. Such antibody fragments include, for example, Fab, F(ab')$_2$, Fv, single-chain Fv (scFv) which comprises a heavy chain Fv and a light chain Fv coupled together with an appropriate linker, diabody (diabodies), linear antibodies, and multispecific antibodies prepared from antibody fragments. Previously, antibody fragments were produced by digesting natural antibodies with a protease; currently, methods for expressing them as recombinant antibodies using genetic engineering techniques are also known (see Morimoto et al., *Journal of Biochemical and Biophysical Methods* 24:107-117 (1992); Brennan et al., *Science* 229:81 (1985); Co, M. S. et al., *J. Immunol.*, 1994, 152, 2968-2976; Better, M. & Horwitz, A. H., *Methods in Enzymology*, 1989, 178, 476-496, Academic Press, Inc.; Plueckthun, A. & Skerra, A., *Methods in Enzymology*, 1989, 178, 476-496, Academic Press, Inc.; Lamoyi, E., *Methods in Enzymology*, 1989, 121, 663-669; Bird, R. E. et al., *TIBTECH*, 1991, 9, 132-137).

An "Fv" fragment is the smallest antibody fragment, and contains a complete antigen recognition site and a binding site. This region is a dimer ($V_H$-$V_L$ dimer) wherein the variable regions of each of the heavy chain and light chain are strongly connected by a noncovalent bond. The three CDRs of each of the variable regions interact with each other to form an antigen-binding site on the surface of the $V_H$-$V_L$ dimer. In other words, a total of six CDRs from the heavy and light chains function together as an antibody's antigen-binding site. However, a variable region (or a half Fv, which contains only three antigen-specific CDRS) alone is also known to be able to recognize and bind to an antigen, although its affinity is lower than the affinity of the entire binding site. Thus, a preferred antibody fragment of the present invention is an Fv fragment, but is not limited thereto. Such an antibody fragment may be a polypeptide which comprises an antibody fragment of heavy or light chain CDRs which are conserved, and which can recognize and bind its antigen.

A Fab fragment (also referred to as F(ab)) also contains a light chain constant region and heavy chain constant region (CH1). For example, papain digestion of an antibody produces the two kinds of fragments: an antigen-binding fragment, called a Fab fragment, containing the variable regions of a heavy chain and light chain, which serve as a single antigen-binding domain; and the remaining portion, which is called an "Fc" because it is readily crystallized. A Fab' fragment is different from a Fab fragment in that a Fab' fragment also has several residues derived from the carboxyl terminus of a heavy chain CH1 region, which contains one or more cysteine residues from the hinge region of an antibody. A Fab' fragment is, however, structurally equivalent to Fab in that both are antigen-binding fragments which comprise the variable regions of a heavy chain and light chain, which serve as a single antigen-binding domain. Herein, an antigen-binding fragment comprising the variable regions of a heavy chain and light chain which serve as a single antigen-binding domain, and which is equivalent to that obtained by papain digestion, is referred to as a "Fab-like antibody," even when it is not identical to an antibody fragment produced by protease digestion. Fab'-SH is Fab' with one or more cysteine residues having free thiol groups in its constant region. A F(ab') fragment is produced by cleaving the disulfide bond between the cysteine residues in the hinge region of F(ab')$_2$. Other chemically crosslinked antibody fragments are also known to those skilled in the art. Pepsin digestion of an antibody yields two fragments; one is a F(ab')$_2$ fragment which comprises two antigen-binding domains and can cross-react with antigens, and the other is the remaining fragment (referred to as pFc'). Herein, an antibody fragment equivalent to that obtained by pepsin digestion is referred to as a "F(ab')$_2$-like antibody" when it comprises two antigen-binding domains and can cross-react with antigens. Such antibody fragments can also be produced, for example, by genetic engineering. Such antibody fragments can also be isolated, for example, from the antibody phage library described above. Alternatively, F(ab)$_2$-SH fragments can be recovered directly from hosts, such as *E. coli*, and then allowed to form F(ab')$_2$ fragments by chemical crosslinking (Carter et al., Bio/Technology 10:163-167 (1992)). In an alternative method, F(ab')$_2$ fragments can be isolated directly from a culture of recombinant hosts.

The term "diabody (Db)" refers to a bivalent antibody fragment constructed by gene fusion (for example, P. Holliger et al., *Proc. Natl. Acad. Sci. USA* 90: 6444-6448 (1993), EP 404,097, WO 93/11161). In general, a diabody is a dimer of two polypeptide chains. In the each of the polypeptide chains, a light chain variable region ($V_L$) and a heavy chain variable region ($V_H$) in an identical chain are connected via a short linker, for example, a linker of about five residues, so that they cannot bind together. Because the linker between the two is too short, the $V_L$ and $V_H$ in the same polypeptide chain cannot form a single chain V region fragment, but instead form a dimer. Thus, a diabody has two antigen-binding domains. When the $V_L$ and $V_H$ regions against the two types of antigens (a and b) are combined to form $V_{La}$-$V_{Hb}$ and $V_{Lb}$-$V_{Ha}$ via a linker of about five residues, and then co-expressed, they are secreted as bispecific Dbs. The antibodies of the present invention may be such Dbs.

A single-chain antibody (also referred to as "scFv") can be prepared by linking a heavy chain V region and a light chain V region of an antibody (for a review of scFv see Pluckthun "The Pharmacology of Monoclonal Antibodies" Vol. 113, eds. Rosenburg and Moore, Springer Verlag, N.Y., pp. 269-315 (1994)). Methods for preparing single-chain antibodies are known in the art (see, for example, U.S. Pat. Nos. 4,946,778; 5,260,203; 5,091,513; and 5,455,030). In such scFvs, the heavy chain V region and the light chain V region are linked together via a linker, preferably, a polypeptide linker (Huston, J. S. et al., *Proc. Natl. Acad. Sci. U.S.A*, 1988, 85, 5879-5883). The heavy chain V region and the light chain V region in a scFv may be derived from the same antibody, or from different antibodies. The peptide linker used to ligate the V regions may be any single-chain peptide consisting of 12 to 19 residues. A DNA encoding a scFv can be amplified by PCR using, as a template, either the entire DNA, or a partial DNA encoding a desired amino acid sequence, selected from a DNA encoding the heavy chain or the V region of the heavy chain of the above antibody, and a DNA encoding the light chain or the V region of the light chain of the above antibody; and using a primer pair that defines the two ends. Further amplification can be subsequently conducted using a combination of the DNA encoding the peptide linker portion, and the primer pair that defines both ends of the DNA to be ligated to the heavy and light chain respectively. After constructing DNAs encoding scFvs, conventional methods can be used to obtain expression vectors comprising these DNAs, and hosts transformed by these expression vectors. Furthermore, scFvs can be obtained according to conventional methods using the resulting hosts. These antibody fragments can be produced in hosts by obtaining genes that encode the antibody fragments and expressing these as outlined above. Antibodies bound to various types of molecules, such as polyethylene glycols (PEGs), may be used as modified antibodies. Methods for modifying antibodies are already established in the art. The term "antibody" in the present invention also encompasses the above-described antibodies.

The antibodies obtained can be purified to homogeneity. The antibodies can be isolated and purified by a method routinely used to isolate and purify proteins. The antibodies can be isolated and purified by the combined use of one or more methods appropriately selected from column chromatography, filtration, ultrafiltration, salting out, dialysis, preparative polyacrylamide gel electrophoresis, and isoelectrofocusing, for example (Strategies for Protein Purification and Characterization: A Laboratory Course Manual, Daniel R. Marshak et al. eds., Cold Spring Harbor Laboratory Press (1996); Antibodies.: A Laboratory Manual. Ed Harlow and David Lane, Cold Spring Harbor Laboratory, 1988). Such methods are not limited to those listed above. Chromatographic methods include affinity chromatography, ion exchange chromatography, hydrophobic chromatography, gel filtration, reverse-phase chromatography, and adsorption chromatography. These chromatographic methods can be practiced using liquid phase chromatography, such as HPLC and FPLC. Columns to be used in affinity chromatography include protein A columns and protein G columns. For example, protein A columns include Hyper D, POROS, and Sepharose F. F. (Pharmacia). Antibodies can also be purified by utilizing antigen binding, using carriers on which antigens have been immobilized.

The antibodies of the present invention can be formulated according to standard methods (see, for example, Remington's Pharmaceutical Science, latest edition, Mark Publishing Company, Easton, U.S.A), and may comprise pharmaceutically acceptable carriers and/or additives. The present invention relates to compositions (including reagents and pharmaceuticals) comprising the antibodies of the invention, and pharmaceutically acceptable carriers and/or additives. Exemplary carriers include surfactants (for example, PEG and Tween), excipients, antioxidants (for example, ascorbic acid), coloring agents, flavoring agents, preservatives, stabilizers, buffering agents (for example, phosphoric acid, citric acid, and other organic acids), chelating agents (for example, EDTA), suspending agents, isotonizing agents, binders, disintegrators, lubricants, fluidity promoters, and corrigents. However, the carriers that may be employed in the present invention are not limited to this list. In fact, other commonly used carriers can be appropriately employed: light anhydrous silicic acid, lactose, crystalline cellulose, mannitol, starch, carmelose calcium, carmelose sodium, hydroxypropylcellulose, hydroxypropylmethyl cellulose, polyvinylacetaldiethylaminoacetate, polyvinylpyrrolidone, gelatin, medium chain fatty acid triglyceride, polyoxyethylene hydrogenated castor oil 60, sucrose, carboxymethylcellulose, corn starch, inorganic salt, and so on. The composition may also comprise other low-molecular-weight polypeptides, proteins such as serum albumin, gelatin, and immunoglobulin, and amino acids such as glycine, glutamine, asparagine, arginine, and lysine. When the composition is prepared as an aqueous solution for injection, it can comprise an isotonic solution comprising, for example, physiological saline, dextrose, and other adjuvants, including, for example, D-sorbitol, D-mannose, D-mannitol, and sodium chloride, which can also contain an appropriate solubilizing agent, for example, alcohol (for example, ethanol), polyalcohol (for example, propylene glycol and PEG), and non-ionic detergent (polysorbate 80 and HCO-50).

If necessary, antibodies of the present invention may be encapsulated in microcapsules (microcapsules made of hydroxycellulose, gelatin, polymethylmethacrylate, and the like), and made into components of colloidal drug delivery systems (liposomes, albumin microspheres, microemulsions, nano-particles, and nano-capsules) (for example, see "Remington's Pharmaceutical Science 16th edition", Oslo Ed. (1980)). Moreover, methods for making sustained-release drugs are known, and these can be applied for the antibodies of the present invention (Langer et al., *J. Biomed. Mater. Res.* 15: 167-277 (1981); Langer, Chem. Tech. 12: 98-105 (1982); U.S. Pat. No. 3,773,919; EP Patent Application No. 58,481; Sidman et al., Biopolymers 22: 547-556 (1983); EP: 133,988).

An "immune response" refers to a humoral immune response and/or cellular immune response leading to the activation or proliferation of B- and/or T-lymphocytes and/or and antigen presenting cells. In some instances, however, the immune responses may be of low intensity and become detectable only when using at least one substance in accordance with the invention "Immunogenic" refers to an agent used to stimulate the immune system of a living organism, so that one or more functions of the immune system are increased and directed towards the immunogenic agent. An "immunogenic polypeptide" is a polypeptide that elicits a cellular and/or humoral immune response, whether alone or linked to a carrier in the presence or absence of an adjuvant. Preferably, antigen presenting cell may be activated.

A substance that "enhances" an immune response refers to a substance in which an immune response is observed that is greater or intensified or deviated in any way with the addition of the substance when compared to the same immune response measured without the addition of the substance. For example, the lytic activity of cytotoxic T cells can be measured, e.g. using a $^{51}$Cr release assay, in samples obtained with and without the use of the substance during immunization. The amount of the substance at which the CTL lytic activity is enhanced as compared to the CTL lytic activity without the substance is said to be an amount sufficient to enhance the immune response of the animal to the antigen. In certain embodiments, the immune response in enhanced by a factor of at least about 2, such as by a factor of about 3 or more. The amount or type of cytokines secreted may also be altered. Alternatively, the amount of antibodies induced or their subclasses may be altered.

The terms "immunize" or "immunization" or related terms refer to conferring the ability to mount a substantial immune response (comprising antibodies and/or cellular immunity such as effector CTL) against a target antigen or epitope. These terms do not require that complete immunity be created, but rather that an immune response be produced which is substantially greater than baseline. For example, a mammal may be considered to be immunized against a target antigen if the cellular and/or humoral immune response to the target antigen occurs following the application of methods of the invention.

The term "immunotherapeutic" refers to a composition for the treatment of diseases, disorders or conditions. More specifically, the term is used to refer to a method of treatment wherein a beneficial immune response is generated by vaccination or by transfer of immune molecules. An "immunologically effective amount" refers to an amount of a composition sufficient to induce an immune response in an individual when introduced into that individual. In the context of active immunization, the term is synonymous with "immunogenically effective amount." The amount of a composition necessary to be immunologically effective varies according many factors including to the composition, the presence of other components in the composition (e.g. adjuvants), the antigen, the route of immunization, the individual, the prior immune or physiologic state etc.

Nucleic Acid Molecules, Expression Cassettes and Expression Vectors

The AREs and conjugated compounds can be encoded by a nucleic acid sequence, and the nucleic acid sequence can also include a promoter. The nucleic acid sequence can also include a polyadenylation signal. In some embodiments, the polyadenylation signal is a synthetic minimal polyadenylation signal or a sequence of six Ts.

The term "nucleic acid" refers to deoxyribonucleic acid (DNA) or ribonucleic acid (RNA) and polymers thereof in either single- or double-stranded form, composed of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues. A "nucleic acid fragment" is a portion of a given nucleic acid molecule.

A "nucleotide sequence" is a polymer of DNA or RNA that can be single-stranded or double-stranded, optionally containing synthetic, non-natural or altered nucleotide bases capable of incorporation into DNA or RNA polymers.

The terms "nucleic acid," "nucleic acid molecule," "nucleic acid fragment," "nucleic acid sequence or segment," or "polynucleotide" are used interchangeably and may also be used interchangeably with gene, cDNA, DNA and RNA encoded by a gene.

The invention encompasses isolated or substantially purified nucleic acid nucleic acid molecules and compositions containing those molecules. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule or biologically active portion thereof, is substantially free of other cellular material, or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. Fragments and variants of the disclosed nucleotide sequences are also encompassed by the present invention. By "fragment" or "portion" is meant a full length or less than full length of the nucleotide sequence.

"Naturally occurring," "native," or "wild-type" is used to describe an object that can be found in nature as distinct from being artificially produced. For example, a protein or nucleotide sequence present in an organism (including a virus), which can be isolated from a source in nature and that has not been intentionally modified by a person in the laboratory, is naturally occurring.

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence.

A "transgene" refers to a gene that has been introduced into the genome by transformation. Transgenes include, for example, DNA that is either heterologous or homologous to the DNA of a particular cell to be transformed. Additionally, transgenes may include native genes inserted into a non-native organism, or chimeric genes.

The term "endogenous gene" refers to a native gene in its natural location in the genome of an organism.

The terms "protein," "peptide" and "polypeptide" are used interchangeably herein.

"Wild-type" refers to the normal gene or organism found in nature.

"Genome" refers to the complete genetic material of an organism.

A "vector" is defined to include, inter alia, any viral vector, as well as any plasmid, cosmid, phage or binary vector in double or single stranded linear or circular form that may or may not be self transmissible or mobilizable, and that can transform prokaryotic or eukaryotic host either by integration into the cellular genome or exist extrachromosomally (e.g., autonomous replicating plasmid with an origin of replication).

"Expression cassette" as used herein means a nucleic acid sequence capable of directing expression of a particular nucleotide sequence in an appropriate host cell, which may include a promoter operably linked to the nucleotide sequence of interest that may be operably linked to termination signals. The coding region usually codes for a functional RNA of interest, for example an RNA encoding an epitope or conjugated compound. The expression cassette including the nucleotide sequence of interest may be chimeric. The expression cassette may also be one that is naturally occurring but has been obtained in a recombinant form useful for heterologous expression. The expression of the nucleotide sequence in the expression cassette may be under the control of a constitutive promoter or of a regulatable promoter that initiates transcription only when the host cell is exposed to some particular stimulus. In the case of a multicellular organism, the promoter can also be specific to a particular tissue or organ or stage of development.

Such expression cassettes can include a transcriptional initiation region linked to a nucleotide sequence of interest. Such an expression cassette is provided with a plurality of restriction sites for insertion of the gene of interest to be under the transcriptional regulation of the regulatory regions.

"Regulatory sequences" are nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences that may be a combination of synthetic and natural sequences. As is noted herein, the term "suitable regulatory sequences" is not limited to promoters. However, some suitable regulatory sequences useful in the present invention will include, but are not limited to constitutive promoters, tissue-specific promoters, development-specific promoters, regulatable promoters and viral promoters.

"Promoter" refers to a nucleotide sequence, usually upstream (5') to its coding sequence, which directs and/or controls the expression of the coding sequence by providing the recognition for RNA polymerase and other factors required for proper transcription. "Promoter" includes a minimal promoter that is a short DNA sequence comprised of a TATA-box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence that can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors that control the effectiveness of transcription initiation in response to physiological or developmental conditions. Examples of promoters that may be used in the present invention include the mouse U6 RNA promoters, synthetic human H1RNA promoters, SV40, CMV, RSV, RNA polymerase II and RNA polymerase III promoters.

The "initiation site" is the position surrounding the first nucleotide that is part of the transcribed sequence, which is also defined as position +1. With respect to this site all other sequences of the gene and its controlling regions are numbered. Downstream sequences (i.e., further protein encoding sequences in the 3' direction) are denominated positive, while upstream sequences (mostly of the controlling regions in the 5' direction) are denominated negative.

Promoter elements, particularly a TATA element, that are inactive or that have greatly reduced promoter activity in the absence of upstream activation are referred to as "minimal or core promoters." In the presence of a suitable transcription factor, the minimal promoter functions to permit transcription. A "minimal or core promoter" thus consists only of all basal elements needed for transcription initiation, e.g., a TATA box and/or an initiator.

"Constitutive expression" refers to expression using a constitutive or regulated promoter. "Conditional" and "regulated expression" refer to expression controlled by a regulated promoter.

"Operably-linked" refers to the association of nucleic acid sequences on single nucleic acid fragment so that the function of one of the sequences is affected by another. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i.e., that the coding sequence or functional RNA is under the transcriptional control of the promoter). Coding sequences can be operably-linked to regulatory sequences in sense or antisense orientation.

"Expression" refers to the transcription and/or translation of an endogenous gene, heterologous gene or nucleic acid segment, or a transgene in cells. For example, in the case of epitope constructs, expression may refer to the transcription of the epitope only. In addition, expression refers to the transcription and stable accumulation of sense (mRNA) or functional RNA. Expression may also refer to the production of protein.

The term "transformation" refers to the transfer of a nucleic acid fragment into the genome of a host cell, resulting in genetically stable inheritance. A "host cell" is a cell that has been transformed, or is capable of transformation, by an exogenous nucleic acid molecule. Host cells containing the transformed nucleic acid fragments are referred to as "transgenic" cells.

"Transformed," "transduced," "transgenic" and "recombinant" refer to a host cell into which a heterologous nucleic acid molecule has been introduced. As used herein the term "transfection" refers to the delivery of DNA into eukaryotic (e.g., mammalian) cells. The term "transformation" is used herein to refer to delivery of DNA into prokaryotic (e.g., E. coli) cells. The term "transduction" is used herein to refer to infecting cells with viral particles. The nucleic acid molecule can be stably integrated into the genome generally known in the art. Known methods of PCR include, but are not limited to, methods using paired primers, nested primers, single specific primers, degenerate primers, gene-specific primers, vector-specific primers, partially mismatched primers, and the like. For example, "transformed," "transformant," and "transgenic" cells have been through the transformation process and contain a foreign gene integrated into their chromosome. The term "untransformed" refers to normal cells that have not been through the transformation process.

"Genetically altered cells" denotes cells which have been modified by the introduction of recombinant or heterologous nucleic acids (e.g., one or more DNA constructs or their RNA counterparts) and further includes the progeny of such cells which retain part or all of such genetic modification.

Nucleic Acid Molecules of the Invention

The terms "isolated and/or purified" refer to in vitro isolation of a nucleic acid, e.g., a DNA or RNA molecule from its natural cellular environment, and from association with other components of the cell, such as nucleic acid or polypeptide, so that it can be sequenced, replicated, and/or expressed. The RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid.

As used herein, the term "recombinant nucleic acid", e.g., "recombinant DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source would be a DNA sequence that is identified as a useful fragment within a given organism, and which is then chemically synthesized in essentially pure form. An example of such DNA "isolated" from a source would be a useful DNA sequence that is excised or removed from a source by chemical means, e.g., by the use of restriction endonucleases, so that it can be further manipulated, e.g., amplified, for use in the invention, by the methodology of genetic engineering. "Recombinant DNA" includes completely synthetic DNA sequences, semi synthetic DNA sequences, DNA sequences isolated from biological sources, and DNA sequences derived from RNA, as well as mixtures thereof.

Expression Cassettes of the Invention

To prepare expression cassettes, the recombinant DNA sequence or segment may be circular or linear, double-stranded or single-stranded. Generally, the DNA sequence or segment is in the form of chimeric DNA, such as plasmid DNA or a vector that can also contain coding regions flanked by control sequences that promote the expression of the recombinant DNA present in the resultant transformed cell.

A "chimeric" vector or expression cassette, as used herein, means a vector or cassette including nucleic acid sequences from at least two different species, or has a nucleic acid sequence from the same species that is linked or associated in a manner that does not occur in the "native" or wild type of the species.

Aside from recombinant DNA sequences that serve as transcription units for an RNA transcript, or portions thereof, a portion of the recombinant DNA may be untranscribed, serving a regulatory or a structural function. For example, the recombinant DNA may have a promoter that is active in mammalian cells.

Other elements functional in the host cells, such as introns, enhancers, polyadenylation sequences and the like, may also be a part of the recombinant DNA. Such elements may or may not be necessary for the function of the DNA, but may provide improved expression of the DNA by affecting transcription, or the like. Such elements may be included in the DNA as desired to obtain the optimal performance of the RNA in the cell.

Control sequences are DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

Operably linked nucleic acids are nucleic acids placed in a functional relationship with another nucleic acid sequence. For example, a promoter or enhancer is operably linked to a coding sequence if it affects the transcription of the sequence; or a ribosome binding site is operably linked to a coding sequence if it is positioned so as to facilitate translation. Generally, operably linked DNA sequences are DNA sequences that are linked are contiguous. However, enhancers do not have to be contiguous. Linking is accomplished by ligation at convenient restriction sites. If such sites do not exist, the synthetic oligonucleotide adaptors or linkers are used in accord with conventional practice.

The recombinant DNA to be introduced into the cells may contain either a selectable marker gene or a reporter gene or both to facilitate identification and selection of expressing cells from the population of cells sought to be transfected or infected through viral vectors. In other embodiments, the selectable marker may be carried on a separate piece of DNA and used in a co-transfection procedure. Both selectable markers and reporter genes may be flanked with appropriate regulatory sequences to enable expression in the host cells. Useful selectable markers are known in the art and include, for example, antibiotic-resistance genes, such as neo and the like.

Reporter genes are used for identifying potentially transfected cells and for evaluating the functionality of regulatory sequences. Reporter genes that encode for easily assayable proteins are well known in the art. In general, a reporter gene is a gene that is not present in or expressed by the recipient organism or tissue and that encodes a protein whose expression is manifested by some easily detectable property, e.g., enzymatic activity. For example, reporter genes include the chloramphenicol acetyl transferase gene (cat) from Tn9 of *E. coli* and the luciferase gene from firefly *Photinus pyralis*. Expression of the reporter gene is assayed at a suitable time after the DNA has been introduced into the recipient cells.

The general methods for constructing recombinant DNA that can transfect target cells are well known to those skilled in the art, and the same compositions and methods of construction may be utilized to produce the DNA useful herein.

The recombinant DNA can be readily introduced into the host cells, e.g., mammalian, bacterial, yeast or insect cells by transfection with an expression vector composed of DNA encoding the epitope or conjugated compound by any procedure useful for the introduction into a particular cell, e.g., physical or biological methods, to yield a cell having the recombinant DNA stably integrated into its genome or existing as a episomal element, so that the DNA molecules, or sequences of the present invention are expressed by the host cell. Preferably, the DNA is introduced into host cells via a vector. The host cell is preferably of eukaryotic origin, e.g., plant, mammalian, insect, yeast or fungal sources, but host cells of non-eukaryotic origin may also be employed.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. For mammalian gene therapy, as described herein below, it is desirable to use an efficient means of inserting a copy gene into the host genome. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like. See, for example, U.S. Pat. Nos. 5,350,674 and 5,585,362.

As discussed herein, a "transfected" "or "transduced" host cell or cell line is one in which the genome has been altered or augmented by the presence of at least one heterologous or recombinant nucleic acid sequence. The host cells of the present invention are typically produced by transfection with a DNA sequence in a plasmid expression vector, a viral expression vector, or as an isolated linear DNA sequence. The transfected DNA can become a chromosomally integrated recombinant DNA sequence, which is composed of sequence encoding the epitope or conjugated compound.

To confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

To detect and quantitate RNA produced from introduced recombinant DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the recombinant DNA segment in question, they do not provide information as to whether the preselected DNA segment is being expressed. Expression may be evaluated by specifically identifying the peptide products of the introduced recombinant DNA sequences or evaluating the phenotypic changes brought about by the expression of the introduced recombinant DNA segment in the host cell.

Methods for Introducing the Expression Cassettes of the Invention into Cells

The nucleic acid material (e.g., an expression cassette encoding the epitope or conjugated compound) can be introduced into the cell ex vivo or in vivo by genetic transfer methods, such as transfection or transduction, to provide a genetically modified cell. Various expression vectors (i.e., vehicles for facilitating delivery of exogenous nucleic acid into a target cell) are known to one of ordinary skill in the art.

As used herein, "transfection of cells" refers to the acquisition by a cell of new nucleic acid material by incorporation of added DNA. Thus, transfection refers to the insertion of nucleic acid into a cell using physical or chemical methods. Several transfection techniques are known to those of ordinary skill in the art including calcium phosphate DNA co-precipitation, DEAE-dextran, electroporation, cationic liposome-mediated transfection, tungsten particle-facilitated microparticle bombardment, and strontium phosphate DNA co-precipitation.

In contrast, "transduction of cells" refers to the process of transferring nucleic acid into a cell using a DNA or RNA virus. A RNA virus (i.e., a retrovirus) for transferring a nucleic acid into a cell is referred to herein as a transducing chimeric retrovirus. Exogenous nucleic acid material contained within the retrovirus is incorporated into the genome of the transduced cell. A cell that has been transduced with a chimeric DNA virus (e.g., an adenovirus carrying a cDNA encoding a therapeutic agent), will not have the exogenous nucleic acid material incorporated into its genome but will be capable of expressing the exogenous nucleic acid material that is retained extrachromosomally within the cell.

The exogenous nucleic acid material can include the nucleic acid encoding the epitope or conjugated compound together with a promoter to control transcription. The promoter characteristically has a specific nucleotide sequence necessary to initiate transcription. The exogenous nucleic acid material may further include additional sequences (i.e., enhancers) required to obtain the desired gene transcription activity. For the purpose of this discussion an "enhancer" is simply any non-translated DNA sequence that works with the coding sequence (in cis) to change the basal transcription level dictated by the promoter. The exogenous nucleic acid material may be introduced into the cell genome immediately downstream from the promoter so that the promoter and coding sequence are operatively linked so as to permit transcription of the coding sequence. An expression vector can include an exogenous promoter element to control transcription of the inserted exogenous gene. Such exogenous promoters include both constitutive and regulatable promoters.

Naturally-occurring constitutive promoters control the expression of essential cell functions. As a result, a nucleic acid sequence under the control of a constitutive promoter is expressed under all conditions of cell growth. Constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the beta☐-actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others.

Nucleic acid sequences that are under the control of regulatable promoters are expressed only or to a greater or lesser degree in the presence of an inducing or repressing agent, (e.g., transcription under control of the metallothionein promoter is greatly increased in presence of certain metal ions). Regulatable promoters include responsive elements (REs) that stimulate transcription when their inducing factors are bound. For example, there are REs for serum factors, steroid hormones, retinoic acid, cyclic AMP, and tetracycline and doxycycline. Promoters containing a particular RE can be chosen in order to obtain a regulatable response and in some cases, the RE itself may be attached to a different promoter, thereby conferring regulatability to the encoded nucleic acid sequence. Thus, by selecting the appropriate promoter (constitutive versus regulatable; strong versus weak), it is possible to control both the existence and level of expression of a nucleic acid sequence in the genetically modified cell. If the nucleic acid sequence is under the control of an regulatable promoter, delivery of the therapeutic agent in situ is triggered by exposing the genetically modified cell in situ to conditions for permitting transcription of the nucleic acid sequence, e.g., by intraperitoneal injection of specific inducers of the regulatable promoters which control transcription of the agent. For example, in situ expression of a nucleic acid sequence under the control of the metallothionein promoter in genetically modified cells is enhanced by contacting the genetically modified cells with a solution containing the appropriate (i.e., inducing) metal ions in situ.

Accordingly, the amount of RNA generated in situ is regulated by controlling such factors as the nature of the promoter used to direct transcription of the nucleic acid sequence, (i.e., whether the promoter is constitutive or regulatable, strong or weak) and the number of copies of the exogenous nucleic acid sequence encoding the epitope or conjugated compound sequence that are in the cell.

In addition to at least one promoter and at least one heterologous nucleic acid sequence encoding the epitope or conjugated compound sequence, the expression vector may include a selection gene, for example, a neomycin resistance gene, for facilitating selection of cells that have been transfected or transduced with the expression vector.

Cells can also be transfected with two or more expression vectors, at least one vector containing the nucleic acid sequence(s) encoding the epitope or conjugated compound sequence, the other vector containing a selection gene. The selection of a suitable promoter, enhancer, selection gene, and/or signal sequence is deemed to be within the scope of one of ordinary skill in the art without undue experimentation.

The following discussion is directed to various utilities of the instant invention. For example, the instant invention has utility as an expression system suitable for silencing the expression of gene(s) of interest.

The instant invention also provides methods for genetically modifying cells of a mammalian recipient in vivo. According to one embodiment, the method comprises introducing an expression vector for expressing the epitope or conjugated compound sequence in cells of the mammalian recipient in situ by, for example, injecting the vector into the recipient.

Formulations and Methods of Administration

The vaccines and compositions of the invention may be formulated as pharmaceutical compositions and administered to a mammalian host, such as a human patient, in a variety of forms adapted to the chosen route of administration, i.e., orally, intranasally, intradermally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts may be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions that can be used to deliver the compounds of the present invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of the present invention can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of the present invention in a liquid composition, such as a lotion, will be from about 0.1-25 wt-%, preferably from about 0.5-10 wt-%. The concentration in a semi-solid or solid composition such as a gel or a powder will be about 0.1-5 wt-%, preferably about 0.5-2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 µM, preferably, about 1 to 50 µM, most preferably, about 2 to about 30 µM. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Although the foregoing specification and examples fully disclose and enable the present invention, they are not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound comprising at least one antigen covalently linked to an antibody-recognition epitope (ARE), wherein the ARE is a VP-1 epitope of polio virus of about 11-28 amino acids in length comprising IPALTAVETGA (SEQ ID NO: 1) or ALTAVETGAT (SEQ ID NO: 3), wherein the antigen is further conjugated to an antibody to form an antibody:antigen complex and wherein the antigen is an infectious agent antigen or a cancer antigen.

2. The compound of claim 1, wherein the antibody is a chimeric antibody.

3. The compound of claim 2, wherein the antibody is a human antibody or a humanized antibody.

4. The compound of claim 1, wherein a hapten is operably linked to the antigen to form a haptenated antigen.

5. A complex comprising the compound of claim 1 operably linked to a conjugation molecule, wherein the conjugation molecule is a peptide, a nucleic acid, or a polysaccharide that is not the antigen or ARE.

6. A composition comprising the compound of claim 1 and a physiologically-acceptable, non-toxic vehicle.

7. The composition of claim 6, further comprising an adjuvant.

* * * * *